(12) United States Patent  
Updyke et al.

(10) Patent No.: US 9,057,694 B2  
(45) Date of Patent: Jun. 16, 2015

(54) COMPOSITIONS AND METHODS FOR IMPROVING RESOLUTION OF BIOMOLECULES SEPARATED ON POLYACRYLAMIDE GELS

(71) Applicant: Life Technologies Corporation, Carlsbad, CA (US)

(72) Inventors: Timothy Updyke, Temecula, CA (US); Thomas Beardslee, Carlsbad, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 15 days.

(21) Appl. No.: 13/928,137

(22) Filed: Jun. 26, 2013

(65) Prior Publication Data

US 2014/0034500 A1  Feb. 6, 2014

Related U.S. Application Data

(63) Continuation of application No. 11/614,785, filed on Dec. 21, 2006, now abandoned.

(60) Provisional application No. 60/754,328, filed on Dec. 29, 2005, provisional application No. 60/761,342, filed on Jan. 24, 2006.

(51) Int. Cl.
  *G01N 27/447* (2006.01)
  *C07K 1/26* (2006.01)
  *C08J 3/075* (2006.01)
  (Continued)

(52) U.S. Cl.
  CPC ............ *G01N 27/44747* (2013.01); *C07K 1/26* (2013.01); *C08J 3/075* (2013.01); *C08J 2333/26* (2013.01); *C08K 5/0008* (2013.01); *C08L 33/26* (2013.01)

(58) Field of Classification Search
  CPC ................................................ G01N 27/44747
  USPC .................................. 204/450–470, 600–616
  See application file for complete search history.

(56) References Cited

U.S. PATENT DOCUMENTS 4,481,094 A * 11/1984 Fernandez de Castro et al. ............................. 204/468
4,507,233 A   3/1985 Saito
(Continued)

FOREIGN PATENT DOCUMENTS

EP  0339678  11/1989
EP  0555145  11/1993
(Continued)

OTHER PUBLICATIONS

Laemmli, Nature 227, 680-685.*
(Continued)

*Primary Examiner* — Alex Noguerola (57) ABSTRACT

Gels, such as polyacrylamide gels, are provided that include linear polyacrylamide in the stacking gel. Native gels that include linear polyacrylamide in the stacker can be used to separate biomolecular complexes, such as protein complexes. Gel cassettes in which the gap width between front and back plates does not vary by more than 5% at the upper edge of the cassette are also provided. The gel cassettes can be used for electrophoretic separation of proteins and protein complexes on native gels, such as native gels that include linear polyacrylamide in the stacker. The native gels can have multiple wells for electrophoresing at least one sample and/or at least one molecular weight standard.

15 Claims, 3 Drawing Sheets

(51) Int. Cl.
*C08K 5/00* (2006.01)
*C08L 33/26* (2006.01)

(56) References Cited

U.S. PATENT DOCUMENTS

| | | | |
|---|---|---|---|
| 4,657,656 A | | 4/1987 | Ogawa |
| 4,929,329 A | * | 5/1990 | Danby et al. ............... 204/608 |
| 5,059,654 A | | 10/1991 | Hou et al. |
| 5,164,055 A | | 11/1992 | Dubrow |
| 5,212,253 A | | 5/1993 | Ponticello et al. |
| 5,438,092 A | | 8/1995 | Kozulic et al. |
| 5,582,702 A | | 12/1996 | Cabilly et al. |
| 5,660,702 A | | 8/1997 | Starr |
| 5,865,974 A | | 2/1999 | Cabilly et al. |
| 6,379,516 B1 | | 4/2002 | Cabilly et al. |
| 6,464,850 B1 | | 10/2002 | Zhang et al. |
| 6,471,388 B1 | | 10/2002 | Marsh |
| 6,562,213 B1 | | 5/2003 | Cabilly et al. |
| 6,971,758 B2 | | 12/2005 | Inui et al. |
| 7,122,104 B2 | | 10/2006 | Cabilly et al. |
| 2003/0141190 A1 | * | 7/2003 | Alpenfels et al. ............ 204/606 |
| 2003/0157720 A1 | | 8/2003 | Li |
| 2004/0140215 A1 | * | 7/2004 | Panattoni ..................... 204/466 |
| 2007/0151853 A1 | | 7/2007 | Beardslee et al. |

FOREIGN PATENT DOCUMENTS

| | | |
|---|---|---|
| EP | 1979410 | 8/2012 |
| JP | 02-057962 | 2/1990 |
| JP | 05-281189 | 10/1993 |
| JP | 2005-523683 | 5/2011 |
| WO | 2003/034903 | 5/2003 |
| WO | 2004/067155 | 8/2004 |
| WO | 2007/076452 | 7/2007 |

OTHER PUBLICATIONS

Beutler, et al., "Purification of Cachectin", *A Lipoprotien lipase-suppressing hormone secreted b endotoxin-induced raw 264.7 cells*, vol. 161, 1985; pp. 984-995.

Bottari, et al., "Design and Synthesis of Visible Isotope-Coded Affinity Tags for the Absolute Quantification of Specific Proteins in Complex Mixtures", *Bioconjugate Chemistry*, vol. 15, No. 2, Sep. 22, 2003; pp. 380-388.

DELPHION, "The Delphion Integrated View", www.delphion.com/details?pn=US23125232A1&s_Family=1, Oct. 14, 2005; pp. 1-3.

Fehring, et al., "Physical markers for landmarking fluorescently stained gels that facilitate automated spot-picking", *Electrophoresis*, vol. 22, 2001; pp. 2903-2907.

INVITROGEN, "Featuring the Gold Standards in Band Identification", *Protein Standards Brochure*, 2002; 12 pages.

INVITROGEN, "pTrcHis2 A, B, and C, Vectors for Expression of Recombinant Proteins Containing C-Terminal 6xHis Tags in *E. coli*", *Catalog. No. V365-20*, 2001; 17 pages.

Krijt, et al., "Measurement of Homocysteine and Other Aminnothiols in Plasma: Advantages of Using Tris (2-carboxyethyl)phosphine as Reductant Compared with Tri-n-butylphosphine", *Clinical Chemistry*, vol. 47, No. 10, 2001; pp. 1821-1828.

Kulkarni, et al., "Textile Dyes and Dyeing Equipment: Classification, Properties, and Environmental Aspects", *Air and Energy Engineering Research Laboratory*, United States Environmental Protection Agency, Project Summary, Apr. 1985; pp. 1-5.

PCT/US2006/062514; International Search Report and Written Opinion mailed May 23, 2007; 13 pages.

Ramus, et al., "An optimized strategy for ICAT quantification of membrane proteins", *MCP Papers in Press, The American Society for Biochemistry and Molecular Biology, Inc.*, Manuscript M500205-MCP200, Oct. 10, 2005; pp. 1-36.

Sadeghi, et al., "Molecular weight estimation of proteins by gel electrophoresis revisited", *Focus*, vol. 25, No. 3, Oct. 2003; pp. 35-39.

Sato, et al., "Site-Specific Modification of Interleukin-2 by the Combined Use of Genetic Engineering Techniques and Transglutaminase", *Biochemistry*, vol. 35, No. 40, Oct. 8, 1996; pp. 13072-13080.

Schagger, Hermann et al., "Analysis of Molecular masses and Oligomeric States of Protein Complexes by Blue Native Electrophoresis and Isolation of Membrane Protein Complexes by Two-Dimensional Native Electrophoresis.", *Analytical Biochemistry*, vol. 217, 1994; pp. 220-230.

Schurmann, et al., "Cloning of Two Novel ADP-ribosylation Factor-like Proteins and Characterization of Their Differential Expression in 3T3-L1 Cells", *The Journal of Biological Chemistry*, vol. 269, No. 22, Jun. 3, 1994; pp. 15683-15688.

Setlow, "Purification and Properties of Some Unique Low Molecular Weight Basic Proteins Degraded during Germination of *Bacillus megaterium* Spores", *The Journal of Biological Chemistry*, vol. 250, No. 20, Oct. 25, 1975; pp. 8168-8173.

Shimura, et al., "Synthetic oligopeptides as isoelectric point markers for capillary isoelectric focusing with ultraviolet absorption detection", *Electrophoresis*, vol. 21, 2000; pp. 603-610.

Stead, et al., "Characterization of homocysteine metabolism in the rat liver", *Biochem J.*, vol. 350, 2000; pp. 685-692.

Westermark, et al., "Fibril in senile systemic amyloidosis is derived from normal transthyretin", *Proc. Natl. Acad. Sci.*, vol. 87, Apr. 1990; pp. 2843-3845.

Yamagata, et al., "Mapping of phosphorylated proteins on two-dimensional polyacrylamide gels using protein phosphatase", *Proteomics*, vol. 2, 2002; pp. 1267-1276.

EP 06846766.1; Extended European search report mailed Mar. 26, 2009; 7 pgs.

Horowitz, Paul M. et al., "Electrophoresis of Proteins and Nucleic Acids on Acrylamide Agarose Gels Lacking Covalent Cross-Linkings.", *Analytical Biochemistry*, vol. 143, 1984; pp. 333-340.

INVITROGEN, "Rhinohide Polycrylamide Gel Strengthener", *Molecular Probes*, Product Information, May 6, 2005; pp. 1-4.

Schagger, Hermann et al., "Blue Native Electrophoresis for Isolation of Membrane Protein Complexes in Enzymatically Active Form.", *Analytical Biochemistry*, vol. 199, 1991; pp. 223-231.

Schagger, Hermann, "Blue-Native Gels to Isolate Protein Complexes from Mitochondria", *Methods Cell Biol.*, vol. 65, 2001; pp. 232-244.

Schulenberg, et al., "An improved mechanically durable elecrophoresis gel matrix that is fully compatible with fluorescence-based protein detection technologies", *Proteomics*, vol. 3, 2003; pp. 1196-1205.

* cited by examiner

COMPOSITIONS AND METHODS FOR IMPROVING RESOLUTION OF BIOMOLECULES SEPARATED ON POLYACRYLAMIDE GELS

CROSS-REFERENCE TO RELATED APPLICATIONS

This application is a continuation and claims the benefit of U.S. patent application Ser. No. 11/614,785, filed Dec. 21, 2006, now abandoned, which claims benefit of priority to U.S. Provisional Application 60/754,328, entitled "Compositions and Methods for Improving Resolution of Biomolecules Separated on Polyacrylamide Gels", filed on Dec. 29, 2005; and U.S. Provisional Application 60/761,342, entitled "Compositions and Methods for Improving Resolution of Biomolecules Separated on Polyacrylamide Gels", filed Jan. 24, 2006, each of which is herein incorporated by reference in their entirety.

BACKGROUND OF THE INVENTION

1. Field of the Invention

This invention relates to electrophoresis methods and apparatus for minimizing skirting effects in an electrophoretic gel.

2. Background Information

Gel electrophoresis remains a fundamental technique of biochemistry, molecular biology, and cell biology for its usefulness in the separation, characterization, and identification of biomolecules and molecular complexes. Optimal use of gel electrophoresis requires separation of biomolecules with high resolution. One problem confronted by biochemists that employ gel electrophoresis is "skirting", in which molecules of a sample loaded on the gel migrate between the gel and a gel plate, rather than through the gel itself. This leads to the appearance shadow bands that migrate more quickly than the main bands of the biomolecule or complex that migrate within the gel. This creates ambiguity when images of the gel are analyzed, as it is difficult to know whether such bands are artifacts or the result of a low abundance biomolecule or complex.

SUMMARY OF THE INVENTION

Provided herein are electrophoresis gels, cassettes and methods for reducing the skirting effect present in gel electrophoresis. In illustrative embodiments, the electrophoresis gels, cassettes and methods provided herein can be used to reduce the skirting effect present in non-denaturing gel electrophoresis. Also provided herein are electrophoresis gels, cassettes and methods used to reduce the skirting effect present in denaturing gel electrophoresis In one aspect provided herein are electrophoresis gels for the separation of biomolecules wherein the electrophoresis gels have a stacking gel and a separating gel, and wherein the stacking gel includes linear polyacrylamide. In an embodiment of such electrophoresis gels, the electrophoresis gels are polyacrylamide gels, wherein the stacking gel and a separating gel are polyacrylamide gels, and wherein the stacking gel includes linear polyacrylamide. In further or alternative embodiments the acrylamide concentration of the stacking gel is between about 2% and about 6%, while in further or alternative embodiments the acrylamide concentration of the stacking gel is between about 2.5% and about 5%. In further or alternative embodiments, the linear acrylamide concentration of the stacking gel is from about 0.005% to about 1%, while in further or alternative embodiments, the linear acrylamide concentration of the stacking gel is from about 0.01% to about 0.5%. In still further or alternative embodiments, the linear acrylamide concentration of the stacking gel is from about 0.02% to about 0.1%. In other embodiments the separating gel does not comprise linear acrylamide.

In other embodiments of this aspect, the electrophoresis gel is a denaturing gel, while in further or alternative embodiments the electrophoresis gel is a polyacrylamide gel that is a denaturing gel. In further or alternative embodiments, such denaturing gels include sodium dodecyl sulfate (SDS).

In other embodiments of this aspect, the electrophoresis gel is a non-denaturing gel, while in further or alternative embodiments the electrophoresis gel is a polyacrylamide gel that is a non-denaturing gel. In further or alternative embodiments, such non-denaturing gels are gradient gels, while in certain embodiments such non-denaturing gels are Blue Native Gels.

Another aspect provided herein are methods for separating biomolecules on an electrophoresis gel, wherein such methods include applying one or more samples comprising one or more biomolecules to an electrophoresis gel that includes a stacking gel portion and a separating gel portion, wherein the stacking gel portion comprises linear polyacrylamide; and then electrophoretically separating the one or more biomolecules on the electrophoresis gel. In an embodiment of this aspect the separating gel does not comprise linear acrylamide.

In further or alternative embodiments of this aspect, the electrophoresis gel is a denaturing gel, while in further or alternative embodiments the electrophoresis gel is a polyacrylamide gel that is a denaturing gel. In further or alternative embodiments, such denaturing gels include sodium dodecyl sulfate (SDS).

In other embodiments of this aspect, the electrophoresis gel is a non-denaturing gel, while in further or alternative embodiments the electrophoresis gel is a polyacrylamide gel that is a non-denaturing gel. In further or alternative embodiments, such non-denaturing gels are gradient gels, while in certain embodiments such non-denaturing gels are Blue Native Gels.

In other embodiments of this aspect, the methods also include applying one or more molecular weight marker sets to the electrophoresis gel, and in further or alternative embodiments, such methods also include estimating or calculating the molecular weight of one or more biomolecules or biomolecular complexes electrophoreses on the electrophoresis gel.

Another aspect provided herein are gel cassettes for performing gel electrophoresis, wherein the cassette has a consistent gap width across its cross section. In certain embodiments of this aspect such cassettes have a consistent gap width across their upper edge. In certain embodiments of this aspect such cassettes have a consistent gap width across their upper edge in the range from 0.1 millimeters to 5 millimeters. In further or alternative embodiments, the gap width of such cassettes varies by less than 5%, while in other embodiments the variation in the gap width of such cassettes is 2% or less. In further or alternative embodiment, such cassettes contain polyacrylamide gels. In other embodiments, such cassettes are used for performing non-denaturing gel electrophoresis, and the gel is a non-denaturing gel. In certain embodiments, such non-denaturing gels are Blue Native Gels. In further or alternative embodiment, the gels contained in such cassettes are gradient gels. In further or alternative embodiment, such gradient gels are polyacrylamide gradient gels.

In further or alternative embodiments of this aspect, the cassettes are fabricated from plastic, while in further or alternative embodiments the plastic cassettes are fabricated by welding together a front plate to a back plate. In further or alternative embodiments, the welding of the front plate to the back plate results in a cassette with a consistent gap width.

Another aspect provided herein are methods for separating biomolecules on an electrophoresis gel, wherein such methods include applying one or more samples comprising one or more biomolecules to an electrophoresis gel contained in a cassette that has a consistent gap width; and then electrophoretically separating the one or more biomolecules on the electrophoresis gel.

In an embodiment of this aspect the cassette has a consistent gap width across its cross section, while in other embodiments such cassettes have a consistent gap width across their upper edge. In certain embodiments of this aspect such cassettes have a consistent gap width across their upper edge in the range from 0.1 millimeters to 5 millimeters. In further or alternative embodiments, the gap width of such cassettes varies by less than 5%, while in other embodiments the variation in the gap width of such cassettes is 2% or less. In further or alternative embodiment, such cassettes contain polyacrylamide gels. In other embodiments, such cassettes are used for performing non-denaturing gel electrophoresis, and the gel is a non-denaturing gel. In certain embodiments, such non-denaturing gels are Blue Native Gels. In further or alternative embodiment, the gels contained in such cassettes are gradient gels. In further or alternative embodiment, such gradient gels are polyacrylamide gradient gels. In other embodiments of this aspect, the electrophoresis gel contained in such cassettes includes a stacking gel and a separating gel. In further or alternative embodiments, such stacking gels include linear acrylamide.

In further or alternative embodiments of such methods, the method also includes applying one or more molecular weight marker sets to the electrophoresis gel. In further or alternative embodiments, the methods also include estimating or calculating the molecular weight of one or more biomolecules or biomolecular complexes electrophoreses on the electrophoresis gel. In further or alternative embodiments of such methods, the method also includes staining the gel.

DETAILED DESCRIPTION OF THE INVENTION

Disclosed herein are electrophoresis gels, cassettes and methods used for reducing the skirting effect present in gel electrophoresis. In illustrative embodiments, the electrophoresis gels, cassettes and methods provided herein can be used to reduce the skirting effect present in non-denaturing gel electrophoresis, while in other embodiments the electrophoresis gels, cassettes and methods provided herein can be used to reduce the skirting effect present in denaturing gel electrophoresis.

DEFINITIONS

Unless defined otherwise, all technical and scientific terms used herein have the same meaning as commonly understood by one of ordinary skill in the art to which this invention belongs. Generally, the nomenclature used herein are well known and commonly employed in the art. Terms of orientation such as "up" and "down", "top" and "bottom", "above" and "underneath" or "upper" or "lower" and the like refer to orientation of parts during use of a device. Where a term is provided in the singular, the inventors also contemplate the plural of that term. Where there are discrepancies in terms and definitions used in references that are incorporated by reference, the terms used in this application shall have the definitions given herein. As employed throughout the disclosure, the following terms, unless otherwise indicated, shall be understood to have the following meanings The term "ambient temperature" as used herein, refers to the temperature in the range of 20° C. to 25° C.

As used herein, a biopolymer or biomolecule includes, but is not limited to, a nucleic acid, a protein, a polysaccharide, a lipid, and other macromolecules. A nucleic acid includes DNA, RNA, oligonucleotides, and fragments and analogs thereof. Nucleic acid sequences may be derived from genomic DNA, RNA, mitochondrial nucleic acid, chloroplast nucleic acid and other organelles with separate genetic material.

The term "chaotropic agent" or "chaotrope", as used herein, refers to any substance capable of altering the secondary and tertiary structure of proteins and nucleic acids.

The term "electrophoresis gel", as used herein, refers to a gel used for electrophoretic separation of a sample. An electrophoresis gel can be a separating gel only, or an electrophoresis gel can include both a stacking gel and a separating gel.

The term "Linear polyacrylamide" or "linear acrylamide", as used herein, refers to linear, non-crosslinked polymers of acrylamide, and may also be referred to simply as "high molecular weight acrylamide". Linear acrylamide can be in dry chemical or liquid form (i.e., as a weight/volume solution) with molecular weight ranges from 1,000 Daltons to about 6,000,000 Daltons, corresponding to the lengths of the linear polymers.

As used herein, proteins are complex, three-dimensional substances comprising one or more long, folded polypeptide chains. These chains, in turn, include of small chemical units called amino acids. All amino acids contain carbon, hydrogen, oxygen, and nitrogen. Some also contain sulfur. A "peptide" is a compound that includes two or more amino acids. The amino acids link together in a line to form a peptide chain. There are 20 different naturally occurring amino acids involved in the biological production of peptides, and any number of them can be linked in any order to form a peptide chain. The naturally occurring amino acids employed in the biological production of peptides all have the L-configuration. Synthetic peptides can be prepared employing conventional synthetic methods, using L-amino acids, D-amino acids or various combinations of amino acids of the two different configurations. Some peptide chains contain only a few amino acid units. Short peptide chains, e.g., having less than ten amino acid units, are sometimes referred to as "oligopeptides", where the prefix "oligo" signifies "few." Other peptide chains contain a large number of amino acid units, e.g., up to 100 or more, and are referred to a "polypeptides", where the prefix "poly" signifies "many." Still other peptide chains, containing a fixed number of amino acid units are referred to using a prefix that signifies the fixed number of units in the chain, e.g., an octapeptide, where the prefix "octa" signifies eight. (By convention, a "polypeptide" can be considered as any peptide chain containing three or more amino acids, whereas an "oligopeptide" is usually considered as a particular type of "short" polypeptide chain. Thus, as used herein, it is understood that any reference to a "polypeptide" also includes an oligopeptide. Further, any reference to a "peptide" includes polypeptides, oligopeptides. Each different arrangement of amino acids forms a different polypeptide chain. In certain non-limiting examples, the polypeptide includes between 40 and 4000 amino acids, between 50 and 3000 amino acids, or between 75 and 2000 amino acids.

As used herein, a "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogues thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be disclosed herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation. (see Sambrook et al. Molecular Cloning, A Laboratory Manual, Cold Spring Harbor Laboratory Press).

As used herein, non-denaturing gels refer to electrophoresis gels that do not include denaturing agents (such as, for example, denaturing detergents, urea, formamide, and other chaotropes). Non-denaturing (or "native") gels are commonly used in "native" gel electrophoresis, in which the running buffer and sample buffer also lack denaturants. These gels can be particularly useful in investigating molecular interactions, such as for example, protein:protein interactions, protein-nucleic acid interactions, etc. and for performing in-gel activity assays.

The term "polyacrylamide", as used herein, refers to a mixture of acrylamide monomers and N,N'-methylene bis acrylamide ("bis" or "bisacrylamide"), where the acrylamide and bis have been crosslinked to form a branched molecular structure.

The term "sample", as used herein, refers to a mixture of a plurality of unique molecular species which can be separated using gel electrophoresis. By way of example only, a sample may be a mixture of nucleic acids, a mixture of oligonucleotides, a mixture of DNA, a mixture of RNA, or combinations thereof. In addition, by way of example only, a sample may be a mixture of amino acids, a mixture of peptides, a mixture of proteins, or combinations thereof.

The term "separating gel" or, alternatively "body of separating gel" refers to the area of the electrophoresis gel in which the separation of biomolecules occurs and in which separated biomolecules of interest are localized after electrophoretic separation has occurred.

The term "skirting" or "skirting effect", as used herein, refers to when a sample is able to migrate between the electrophoresis gel and the wall of the cassette wall, or the plastic or glass plate or plates, holding or containing the gel. The proportion of sample that is able to migrate between the gel and the cassette wall, or plastic or gel plate(s), migrate faster than rest of the sample thereby giving the appearance of a shadow or skirt band.

Electrophoresis Gels, Compositions and Gel Cassettes for Reducing Skirting Artifacts in Electrophoresis The electrophoresis gels used in the compositions, gel cassettes and methods disclosed herein include a body of separating gel and optionally include a stacking gel. Such separating gels are used to separate sample components including, but not limited to, biomolecules, while the stacking gels are used to help focus the sample components into a narrow band prior to migration into the separating gel. This focusing allows for enhanced resolution of closely migrating sample components. The processes by which the biomolecules separate in the separating gels include, but are not limited to separation by size, separation by charge, or separation by a combination of size and charge. Biomolecules separated using such separating gels are detected by dying, staining or labeling the biomolecules of interest (before, after, or during electrophoretic separation) and observing (visualizing) their position within the separating gel after electrophoretic separation.

In certain embodiments of the compositions, gel cassettes and methods disclosed herein, the dyes, stains, labels or other indicators are added to the sample prior to loading. In other embodiments, the dyes, stains, labels or other indicators are added to the loading well or wells, located in the separating gel or the stacking gel, prior to addition of the sample to such loading well or wells. In other embodiments the dyes, stains, labels or other indicators are added to the loading well or wells after to addition of the sample to the loading well or loading wells. In certain embodiments of the compositions, gel cassettes and methods disclosed herein, the separating gel is exposed to at least one dye, stain, label or other indicator after the electrophoresis run, whereby the sample components become associated with such dyes, stains, labels or other indicators. Alternatively, in certain embodiments of the compositions, gel cassettes and methods disclosed herein, the dyes, stains, labels or other indicators are added to the separation gel whereby they become associated with the sample components during electrophoretic migration. In still other embodiments of the compositions, gel cassettes and methods disclosed herein, the dyes, stains, labels or other indicators are covalently attached to the sample components. Visualization of the sample bands in the separating gel is then achieved by illuminating the separating gel with light of appropriate wavelength(s) to allow observation of the dyes, stains, labels or other indicators associated with the sample bands.

The separating gels of the compositions, gel cassettes and methods disclosed herein can comprise any material which forms a gel including, but not limited to, synthetic polymers, natural polymers and combinations thereof. Examples of such synthetic polymers include, but are not limited to, linear polyacrylamide, crosslinked polyacrylamide, and combinations thereof. Examples of such natural polymers include, but are not limited to, polysaccharides such as agarose. In certain embodiments of the compositions, gel cassettes and methods disclosed herein such separating gels can comprise agarose, polyacrylamide, or combinations of agarose and polyacrylamide. In certain embodiments such separating gels can comprise agarose, polyacrylamide, or combinations of agarose and polyacrylamide. In certain embodiments the separating gels can comprise linear acrylamide and agarose, linear acrylamide and polyacrylamide, or linear acrylamide and a combination of agarose and polyacrylamide.

The stacking gels of the compositions, gel cassettes and methods disclosed herein can comprise any material which forms a gel including, but not limited to, synthetic polymers, natural polymers and combinations thereof. Examples of such synthetic polymers include, but are not limited to, linear polyacrylamide, crosslinked polyacrylamide or combinations thereof. Examples of such natural polymers include, but are not limited to, polysaccharides such as agarose. In certain embodiments of the compositions, gel cassettes and methods disclosed herein such stacking gels can comprise agarose, polyacrylamide, or combinations of agarose and polyacrylamide. In certain embodiments the stacking gels comprise linear acrylamide and agarose, linear acrylamide and polyacrylamide, or linear acrylamide and a combination of agarose and polyacrylamide.

In certain embodiments of the compositions, gel cassettes and methods described, the electrophoresis gels include a separating gel and a stacking gel, in which the stacking gel includes linear polyacrylamide. The inclusion of linear acrylamide in the stacking gel minimizes or prevents skirting artifacts.

In certain embodiments of the compositions, gel cassettes and methods disclosed herein, the separating and stacking gels are polyacrylamide gels, where the stacking gel also includes linear polyacrylamide. In certain embodiments of the compositions, gel cassettes and methods disclosed herein, the separating and stacking gels are polyacrylamide gels, where the separating gel also includes linear polyacrylamide. In certain embodiments of the compositions, gel cassettes and methods disclosed herein, the separating and stacking gels are polyacrylamide gels, where both the separating gel and the stacking gel include linear polyacrylamide.

The polyacrylamide gels of the compositions, gel cassettes and methods disclosed herein are made using solutions of "acrylamide" that are mixtures of monomeric acrylamide and bisacrylamide. The polymerization of acrylamide and bisacrylamide using polymerization initiators, and if needed catalysts, to produce crosslinked polyacrylamide gel. The ratios of monomeric acrylamide to bisacrylamide used in the mixtures to make the polyacrylamide gels of the compositions, gel cassettes and methods disclosed herein range from about 15:1 to about 50:1. By way of example only, the (monomeric) acrylamide:bisacrylamide ratio in such polyacrylamide gels can be 15:1, 19:1, 24:1, 29:1, 37.5:1, 40:1, 45:1 and 50:1. In certain embodiments disclosed herein, the ratios of (monomeric) acrylamide to bisacrylamide for the analysis of proteins and protein complexes, are in the range from about 19:1 to about 45:1.

In certain embodiments of the electrophoresis gels used in the compositions, gel cassettes and methods disclosed herein the stacking gel comprises polyacrylamide made using the mixtures of acrylamide and bisacrylamide as described above. In certain embodiments, the stacking gel is made with lower acrylamide concentration than that used to make the separating gel. By way of example only, stacking gels can have (w/v) acrylamide concentrations ranging from about 2% to about 8%, from about 2.5% to about 7.5% acrylamide, from about 3% to about 7% acrylamide, from about 3.5% to about 6.5% acrylamide, from about 4% to about 6% acrylamide, from about 4.5% to about 5.5% acrylamide, or from about 2.5% to about 6% acrylamide. By way of example only, stacking gels can have (w/v) acrylamide concentrations ranging from 2% to 8%, from 2.5% to 7.5% acrylamide, from 3% to 7% acrylamide, from 3.5% to 6.5% acrylamide, from t 4% to 6% acrylamide, from 4.5% to 5.5% acrylamide, or from 2.5% to 6% acrylamide.

In certain embodiments, the separating gels and stacking gels (individually or together) of the electrophoresis gels used in the compositions, gel cassettes and methods disclosed herein include linear polyacrylamide. In other embodiments, the polyacrylamide separating gels and polyacrylamide stacking gels (individually or together) of the electrophoresis gels used in the compositions, gel cassettes and methods disclosed herein include linear polyacrylamide. The (w/vol) concentrations of the linear acrylamide included in such gels can range from about 0.005% to about 1%, 0.005% to about 0.75%, 0.005% to about 0.5%, 0.005% to about 0.1%, 0.01% to about 1%, 0.01% to about 0.75%, 0.01% to about 0.5%, 0.01% to about 0.1%, 0.02% to about 1%, 0.02% to about 0.75%, 0.02% to about 0.5%, 0.02% to about 0.2%, or 0.02% to about 0.1%. In illustrative embodiments, the (w/vol) concentrations of the linear acrylamide included in such gels can range from 0.005% to 1%, 0.005% to 0.75%, 0.005% to 0.5%, 0.005% to 0.1%, 0.01% to 1%, 0.01% to 0.75%, 0.01% to 0.5%, 0.01% to 0.1%, 0.02% to 1%, 0.02% to 0.75%, 0.02% to 0.5%, 0.02% to 0.2%, or 0.02% to 0.1%. In addition, the molecular weight of the linear acrylamide included in such gels can range from about 1,000 Daltons to about 6,000,000 Daltons, from about 1,000 Daltons to about 5,000,000 Daltons, from about 1,000 Daltons to about 2,000,000 Daltons, from about 1,000 Daltons to about 1,000,000 Daltons, from about 1,000 Daltons to about 750,000 Daltons, from about 1,000 Daltons to about 500,000 Daltons, from about 1,000 Daltons to about 300,000 Daltons, from about 1,000 Daltons to about 200,000 Daltons, from about 1,000 Daltons to about 100,000 Daltons, from about 1,000 Daltons to about 50,000 Daltons, from about 1,000 Daltons to about 25,000 Daltons, or from about 1,000 Daltons to about 10,000 Daltons. In addition, the molecular weight of the linear acrylamide included in such gels can range from 1,000 Daltons to 6,000,000 Daltons, from 1,000 Daltons to 5,000,000 Daltons, from 1,000 Daltons to 2,000,000 Daltons, from 1,000 Daltons to 1,000,000 Daltons, from 1,000 Daltons to 750,000 Daltons, from 1,000 Daltons to 500,000 Daltons, from 1,000 Daltons to 300,000 Daltons, from 1,000 Daltons to 200,000 Daltons, from 1,000 Daltons to 100,000 Daltons, from 1,000 Daltons to 50,000 Daltons, from 1,000 Daltons to 25,000 Daltons, or from 1,000 Daltons to 10,000 Daltons. A skilled artisan can test linear acrylamide of various molecular weight ranges to determine useful molecular weights for linear polyacrylamide used in stacking gels. In some embodiments, the molecular weight of linear polyacrylamide used in the stacking gel of the electrophoresis gels used in the compositions, gel cassettes and methods disclosed herein is greater than about 10,000 Daltons. In some embodiments, the molecular weight of linear polyacrylamide used in the stacking gel of the electrophoresis gels used in the compositions, gel cassettes and methods disclosed herein is greater than about 100,000 Daltons. In some exemplary embodiments, the molecular weight of linear polyacrylamide used in the stacking gel of the electrophoresis gels used in the compositions, gel cassettes and methods disclosed herein is between about 100,000 Daltons and about 1,000,000 Daltons. In some exemplary embodiments, the molecular weight of linear polyacrylamide used in the stacking gel of the electrophoresis gels used in the compositions, gel cassettes and methods disclosed herein is between about 600,000 Daltons and about 1,000,000 Daltons. In some exemplary embodiments, the molecular weight of linear polyacrylamide used in the stacking gel of the electrophoresis gels used in the compositions, gel cassettes and methods disclosed herein is between 600,000 Daltons and 1,000,000 Daltons.

In certain embodiments, the polyacrylamide separating gels and polyacrylamide stacking gels that include linear acrylamide, as disclosed herein, are made by the polymerization of a mixture that includes at least the following mixture of linear acrylamide, monomeric acrylamide, bisacrylamide crosslinker, and a polymerization initiator or initiators. This mixture can optionally include a catalyst. Polymerization of such mixtures can be initiated by any suitable means which are well known to those skilled in the art including, chemical initiation by adding suitable agents and optional catalysts; photochemical initiation using a photoinitiator followed by irradiation at a suitable wavelength; thermal initiation, and combinations thereof. Polymerization of such mixtures incorporates the linear acrylamide into the polymerized gel; thereby strengthening the gel. In addition, the incorporation of linear acrylamide into the stacking gel reduces or eliminates the skirting effect.

The chemical initiators that can be used to initiate the polymerization of such mixtures includes, but are not limited to ammonium persulfate, ammonium persulfate and tetramethylethylenediamine (TEMED) mixtures, sodium persulfate, sodium persulfate and tetramethylethylenediamine (TEMED) mixtures, potassium persulfate, potassium persulfate and tetramethylethylenediamine mixtures, peroxides, benzyl peroxide, dicumyl peroxide, azobis[2-(2-imidazolin-2-yl) propane] HCl (AZIP), azobis(2-amidinopropane) HCl (AZAP), 4,4'-azo-bis-4-cyanopentanoic acid, azobisisobutyramide; azobisisobutyramidine.2HCl, 2-2'-azo-bis-2-(methylcarboxy) propane, 2-hydroxy-1-[4-(hydroxyethoxy) phenyl]-2-methyl-1-propanone, and 2-hydroxy-2-methyl-1-phenyl-1-propanone. The photoinitiators that can be used to initiate the polymerization of such mixtures includes, but are not limited to, acetophenones, benzophenones, multi-ringed quinones, fluoresceins, azobisnitriles, benzoquinones, xanthophenones, benzoins, xanthones, fluoroenones, anthroquinones, eosin, erythrosin, nitroxides, ribolflavin, riboflavin 5'-phosphate, and derivatives thereof.

In certain embodiments, the linear acrylamide is added to a monomeric acrylamide solution prior to adding bisacrylamide crosslinker, initiator(s), and optional catalyzing agent(s), thereby resulting in the mixture of linear acrylamide, monomeric acrylamide, bisacrylamide crosslinker, polymerization initiator(s) and optional catalyst (s) used to make polyacrylamide separating gels and polyacrylamide stacking gels that includes linear acrylamide as disclosed herein. In certain embodiments, the linear acrylamide is added to a monomeric acrylamide solution prior to adding bisacrylamide crosslinker, ammonium persulfate and tetramethylethylenediamine (TEMED), thereby resulting in the mixture used to make polyacrylamide separating gels and polyacrylamide stacking gels that includes linear acrylamide as disclosed herein.

In certain embodiments, the linear acrylamide is added to a solution of monomeric acrylamide solution and bisacrylamide crosslinker prior to adding initiator(s) and optional catalyzing agent(s), thereby resulting in the mixture of linear acrylamide, monomeric acrylamide, bisacrylamide crosslinker, polymerization initiator(s) and a catalyst (s) used to make polyacrylamide separating gels and polyacrylamide stacking gels that includes linear acrylamide as disclosed herein. In certain embodiments, the linear acrylamide is added to a solution of monomeric acrylamide solution and bisacrylamide crosslinker prior to adding ammonium persulfate and tetramethylethylenediamine (TEMED), thereby resulting in the mixture used to make polyacrylamide separating gels and polyacrylamide stacking gels that includes linear acrylamide as disclosed herein.

In certain embodiments, the linear acrylamide is added to a solution of monomeric acrylamide solution, bisacrylamide crosslinker, initiator(s), and optional catalyzing agent(s), thereby resulting in the mixture of linear acrylamide, monomeric acrylamide, bisacrylamide crosslinker, polymerization initiator(s) and optional catalyst (s) used to make polyacrylamide separating gels and polyacrylamide stacking gels that includes linear acrylamide as disclosed herein. In certain embodiments, the linear acrylamide is added to a solution of monomeric acrylamide, bisacrylamide crosslinker, ammonium persulfate and tetramethylethylenediamine (TEMED), thereby resulting in the mixture used to make polyacrylamide separating gels and polyacrylamide stacking gels that includes linear acrylamide as disclosed herein.

The electrophoresis gels of the compositions, gel cassettes and methods disclosed herein can be gradient separating gels, in which the concentration of the polymer (exclusive of the concentration of any added linear polymer) varies through the separating gel, generally from low concentration at the top of the gel body to high concentration at the bottom of the gel body. The concentration range of the polymer in such gradient separating gels depends on the application, and in particular the size of the molecules to be separated. In certain embodiments such separating gel of the electrophoresis gels used in the compositions, gel cassettes and methods disclosed herein can be gradient polyacrylamide separating gels having a concentration gradient with (w/v) acrylamide concentrations ranging from about 2% to about 30%, from about 2.5% to 25%, from about 3% to about 20%, from about 3% to about 8%, from about 4% to about 16%, from about 3% to about 12%, from about 4% to about 20%, or from about 5% to about 20%. In certain embodiments such separating gel of the electrophoresis gels used in the compositions, gel cassettes and methods disclosed herein can be gradient polyacrylamide separating gels having a concentration gradient with (w/v) acrylamide concentrations ranging from 2% to 30%, from 2.5% to 25%, from 3% to 20%, from 3% to 8%, from 4% to 16%, from 3% to 12%, from 4% to 20%, or from 5% to 20%.

The electrophoresis gels of the compositions, gel cassettes and methods disclosed herein can include both a gradient separating gel and a stacking gel, wherein the concentration of the stacking gel polymer is equal to or less than the lowest concentration of polymer used in the gradient separating gel. In certain embodiments, the electrophoresis gels used in the compositions, gel cassettes and methods disclosed herein includes both a polyacrylamide gradient separating gel and a polyacrylamide stacking gel, wherein the concentration of the acrylamide in the stacking gel is equal to or less than the lowest concentration of acrylamide used in the gradient separating gel. In other embodiments, the electrophoresis gels used in the compositions, gel cassettes and methods disclosed herein includes both a polyacrylamide gradient separating gel and a polyacrylamide stacking gel, wherein the concentration of the acrylamide in the stacking gel is equal to or less than the lowest concentration of acrylamide used in the gradient separating gel, and the stacking gel includes linear polyacrylamide at a (w/v) concentration of from about 0.005% to about 1%, 0.005% to about 0.75%, 0.005% to about 0.5%, 0.005% to about 0.1%, 0.01% to about 1%, 0.01% to about 0.75%, 0.01% to about 0.5%, 0.01% to about 0.1%, 0.02% to about 1%, 0.02% to about 0.75%, 0.02% to about 0.5%, 0.02% to about 0.2% or 0.02% to about 0.1%. In other embodiments, the electrophoresis gels used in the compositions, gel cassettes and methods disclosed herein includes both a polyacrylamide gradient separating gel and a polyacrylamide stacking gel, wherein the concentration of the acrylamide in the stacking gel is equal to or less than the lowest concentration of acrylamide used in the gradient separating gel, and the stacking gel includes linear polyacrylamide at a (w/v) concentration of from 0.005% to 1%, 0.005% to 0.75%, 0.005% to 0.5%, 0.005% to 0.1%, 0.01% to 1%, 0.01% to 0.75%, 0.01% to 0.5%, 0.01% to 0.1%, 0.02% to 1%, 0.02% to 0.75%, 0.02% to 0.5%, 0.02% to 0.2% or 0.02% to 0.1%. In another embodiment, an electrophoresis gels used in the compositions, gel cassettes and methods disclosed herein can include a slab gradient polyacrylamide separating gel comprising a polyacrylamide concentration of 4%-16%, and a polyacrylamide stacking gel with a concentration of 3% polyacrylamide plus 0.05% (weight/volume) of linear polyacrylamide.

The gradient separating gels of the electrophoresis gels used in the compositions, gel cassettes and methods disclosed herein can also include linear acrylamide present in a (w/v) concentration of from about 0.005% to about 1%, 0.005% to about 0.75%, 0.005% to about 0.5%, 0.005% to about 0.1%, 0.01% to about 1%, 0.01% to about 0.75%, 0.01% to about 0.5%, 0.01% to about 0.1%, 0.02% to about 1%, 0.02% to about 0.75%, 0.02% to about 0.5%, 0.02% to about 0.1%, or 0.02% to about 0.1%. In certain embodiments such gradient separating gels include linear acrylamide present in a (w/v) concentration of from 0.005% to 1%, 0.005% to 0.75%, 0.005% to 0.5%, 0.005% to 0.1%, 0.01% to 1%, 0.01% to 0.75%, 0.01% to 0.5%, 0.01% to 0.1%, 0.02% to 1%, 0.02% to 0.75%, 0.02% to 0.5%, 0.02% to 0.1%, or 0.02% to 0.1%. In certain embodiments, such gradient separating gels are polyacrylamide gradient separating gels having a concentration gradient with (w/v) acrylamide concentrations ranging from about 2% to about 30%, from about 2.5% to 25%, from about 3% to about 20%, from about 3% to about 8%, from about 4% to about 16%, from about 3% to about 12%, from about 4% to about 20%, or from about 5% to about 20%. In certain embodiments, such gradient separating gels are polyacrylamide gradient separating gels having a concentration gradient with (w/v) acrylamide concentrations ranging from 2% to 30%, from 2.5% to 25%, from 3% to 20%, from 3% to 8%, from 4% to 16%, from 3% to 12%, from 4% to 20%, or from 5% to 20%.

In more specific aspects of the electrophoresis gels used in the compositions, gel cassettes and methods disclosed herein, the electrophoresis gels comprise a stacking gel and a separating gel, in which linear acrylamide is present only in the stacking gel and is not present in the separating gel. In certain embodiments, such stacking gels and separating gels both comprise polyacrylamide, but only the stacking gel comprises linear acrylamide. The addition of linear acrylamide in the separating gel can potentially affect the transparency of the separating gel and thereby affect the detection of sample bands located in the separating gel. Such affects are also known as "clouding" effects.

In certain embodiments, the polyacrylamide stacking gel contains the lowest concentration of acrylamide, with respect to the acrylamide concentration range of the polyacrylamide separating gel. In embodiments where the total acrylamide (acrylamide: bisacrylamide) concentration is below about 3.5% (w/v), the resulting polyacrylamide matrix is a soft gel that, in addition to being prone to breakage, may also result in skirting artifacts. The inclusion of linear polyacrylamide in such low percentage acrylamide stacking gels can improve the strength of the gels and may also reduce or eliminate the occurrence of skirting artifacts.

The electrophoresis gels used in the compositions, gel cassettes and methods can include separating gels that are non-denaturing gels. In certain embodiments such non-denaturing separating gels comprise linear polyacrylamide, while in other embodiments such non-denaturing separating gels are polyacrylamide separating gels that comprise linear polyacrylamide.

The electrophoresis gels used in the compositions, gel cassettes and methods disclosed herein can include stacking gels that are non-denaturing gels. In certain embodiments such non-denaturing stacking gels comprise linear polyacrylamide, while in other embodiments such non-denaturing stacking gels are polyacrylamide stacking gels that comprise linear polyacrylamide.

The electrophoresis gels used in the compositions, gel cassettes and methods disclosed herein can include both separating gels and stacking gels that are non-denaturing gels. In certain embodiments such non-denaturing separating gels and stacking gels comprise linear polyacrylamide, while in other embodiments such non-denaturing separating gels and stacking gels are polyacrylamide separating gels and stacking gels, wherein the stacking gel comprises linear polyacrylamide. In other embodiments such non-denaturing separating gels and stacking gels are polyacrylamide separating gels and stacking gels that comprise linear polyacrylamide.

An example of non-denaturing gels used to separate proteins and protein complexes are Blue native gels ("BN gels"). Such BN gels have been described by Schagger H and von Jagow G (1991) "Blue native electrophoresis for isolation of membrane protein complexes in enzymatically active form" Anal. Biochem. 199: 223-231; Schagger H, Cramer W A, and von Jagow G (1994) "Analysis of molecular masses and oligomeric states of protein complexes by blue native electrophoresis and isolation of membrane protein complexes by two-dimensional native electrophoresis" Anal. Biochem. 217: 220-230; and Schagger H (2001) "Blue-native gels to isolate protein complexes from mitochondria" Methods Cell Biol. 65: 231-244, each of which is herein incorporated by reference in its entireties. Briefly, in BN gels proteins are stained with Coomassie G-250 which confers a negative charge to the proteins without denaturing the proteins. This charge-shifting of proteins by Coomassie G-250 results in proteins being resolved on such "blue-native gels" based upon their size, thereby making accurate size estimation of native proteins and protein complexes possible.

In certain embodiments of the electrophoresis gels used in the compositions, gel cassettes and methods disclosed herein, such electrophoresis gels are non-denaturing Blue Native polyacrylamide gels that include linear polyacrylamide in the stacking gel, and are used for the separation of proteins and protein complexes. In other embodiments, the non-denaturing gels, including BN gels, include gradient separating gels having a concentration gradient with (w/v) acrylamide concentrations ranging from about 2% to about 30%, from about 2.5% to 25%, from about 3% to about 20%, from about 3% to about 8%, from about 4% to about 16%, from about 3% to about 12%, from about 4% to about 20%, or from about 5% to about 20%. In other embodiments, the non-denaturing gels, including BN gels, include gradient separating gels having a concentration gradient with (w/v) acrylamide concentrations ranging from 2% to 30%, from 2.5% to 25%, from 3% to 20%, from 3% to 8%, from 4% to 16%, from 3% to 12%, from 4% to 20%, or from 5% to 20%. In addition, such non-denaturing gels include stacking gels having an acrylamide (w/v) concentration of from about 1% to about 6% in concentration, from about 2% to about 5%, or from about 2.5% to about 4% polyacrylamide. In addition, such non-denaturing gels include stacking gels having an acrylamide (w/v) concentration of from 1% to 6% in concentration, from 2% to 5%, or from 2.5% to 4% polyacrylamide. Such stacking gels also include linear polyacrylamide at a (w/v) concentration of from about 0.005% to about 1%, 0.005% to about 0.75%, 0.005% to about 0.5%, 0.005% to about 0.1%, 0.01% to about 1%, 0.01% to about 0.75%, 0.01% to about 0.5%, 0.01% to about 0.1%, 0.02% to about 1%, 0.02% to about 0.75%, 0.02% to about 0.5%, from about 0.02% to about 0.2%, or 0.02% to about 0.1%. In certain embodiments, such stacking gels also include linear polyacrylamide at a (w/v) concentration of from 0.005% to 1%, 0.005% to 0.75%, 0.005% to 0.5%, 0.005% to 0.1%, 0.01% to 1%, 0.01% to 0.75%, 0.01% to 0.5%, 0.01% to 0.1%, 0.02% to 1%, 0.02% to 0.75%, 0.02% to 0.5%, from 0.02% to 0.2%, or 0.02% to 0.1%.

In certain embodiments the separating gel, which can be a gradient gel, does not include linear acrylamide.

The electrophoresis gels used in the compositions, gel cassettes and methods disclosed herein can be denaturing gels, wherein the gels includes a detergent(s), chaotropic agent(s) or combinations thereof. Chaotropic agents include, but are not limited to, sodium trifluoroacetate, sodium perchlorate, sodium iodide, urea, guanidinium chloride and guanidine isothiocyanate. Denaturing detergents include, but are not limited to, sodium dodecyl sulfate (SDS).

The electrophoresis gels used in the compositions, gel cassettes and methods disclosed herein can include separating gels that are denaturing gels. In certain embodiments such denaturing separating gels comprise linear polyacrylamide, while in other embodiments such denaturing separating gels are polyacrylamide separating gels that comprise linear polyacrylamide.

The electrophoresis gels used in the compositions, gel cassettes and methods disclosed herein can include stacking gels that are denaturing gels. In certain embodiments such denaturing stacking gels comprise linear polyacrylamide, while in other embodiments such denaturing stacking gels are polyacrylamide stacking gels that comprise linear polyacrylamide.

The electrophoresis gels used in the compositions, gel cassettes and methods disclosed herein can include both separating gels and stacking gels that are denaturing gels. In certain embodiments such denaturing separating gels and stacking gels comprise linear polyacrylamide, while in other embodiments such denaturing separating gels and stacking gels are polyacrylamide separating gels and stacking gels, wherein the stacking gel comprises linear polyacrylamide. In other embodiments such denaturing separating gels and stacking gels are polyacrylamide separating gels and stacking gels that comprise linear polyacrylamide.

B. Gel Cassettes Having Consistent Plate-to Plate Spacing Along their Length

Figure 2:
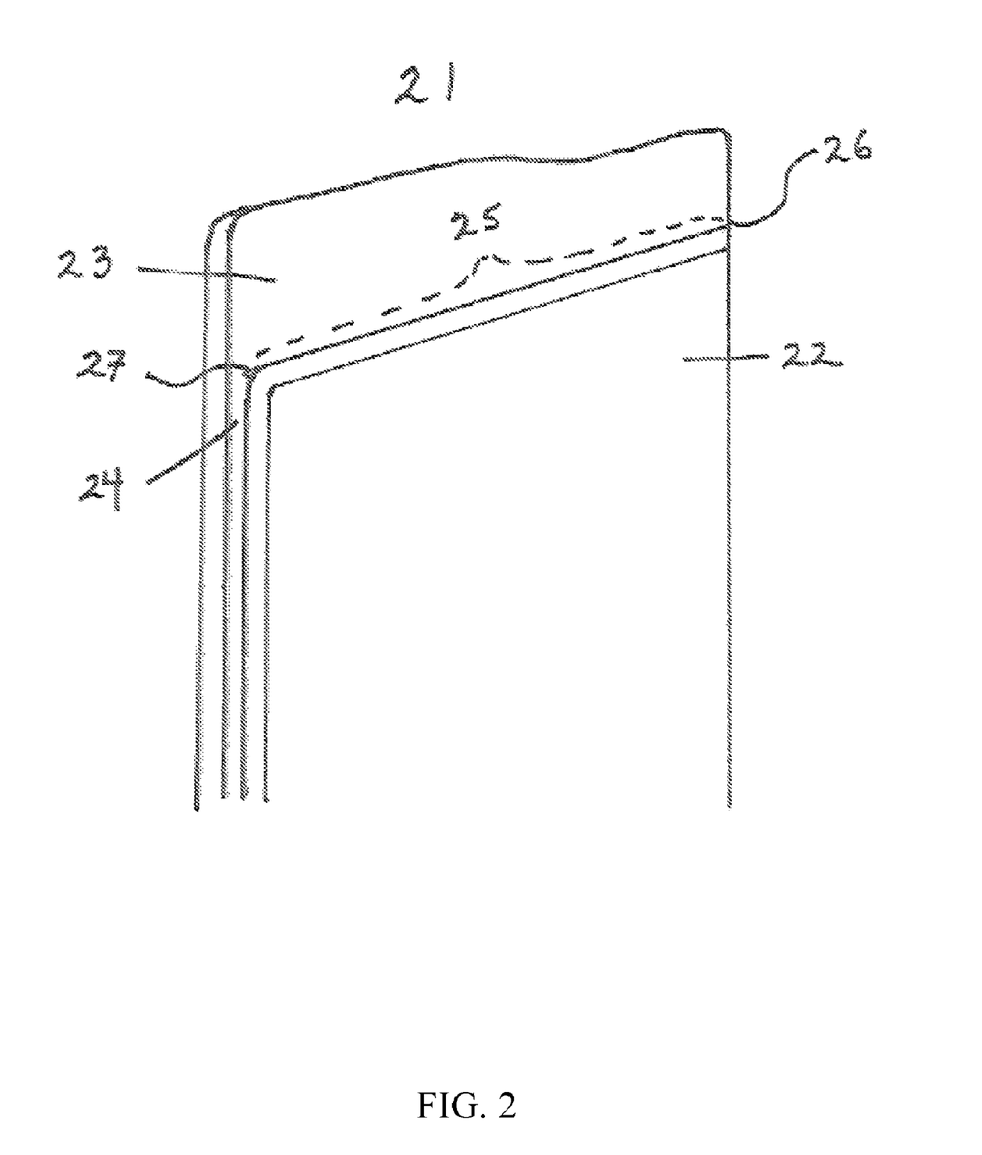
FIG. 2 shows a schematic depiction of a cassette (21) sliced through the middle in which the cassette has a front plate (22) and a back plate (23) with a gap in between (24).

Another aspect of the methods and compositions disclosed herein are gel cassettes that have a consistent internal gap between the front and back plates. For purposes of illustration, FIG. 2 shows a cassette (21) that has been cut down the middle, in which the gap (24) between the back plate (23) and the front plate (22) is substantially the same between a point along the upper edge (25) of the cassette that is in the middle of the cassette (27) and a point along the upper edge (25) of the cassette that is at the outer edge of the cassette (26). A "consistent internal gap between the front and back plates" of a cassette means that the space within a cassette that holds the gel has substantially the same front-to-back depth throughout the space containing the gel. That is, the front-to-back depth at the top edge of the space (the end of the cassette where a comb is inserted to form wells) is substantially the same as the front-to-back depth in the mid-region of the space, the bottom region of the space and the outer edges of the space.

As used herein, "substantially the same" or "substantially equal" means that the internal gap width between plates at the top edge of the cassette (at the end of the cassette where a comb can be inserted) does not vary by more than about 5% of the greatest gap width between an edge of the cassette and the central region of the cassette, and preferably does not vary by more than about 2% of the internal width between the two plates from the edges of the cassette to the mid region of the cassette. In some preferred embodiments, the gap width between the front and back plate does not vary by more than about 1% across the top of the cassette (or the region of the cassette corresponding to where a comb can be inserted to form sample wells). For example, a cassette may be designed to hold a gel of 1 mm thickness, which corresponds to the internal gap width of the cassette. In this case, the width of the internal space of the cassette does not vary by more than about 0.05 mm, by more than about 0.02 mm, or by more than about 0.01 mm across the top of the cassette (or the region of the cassette corresponding to where a comb is inserted). In another example, a cassette may be designed to hold a gel of 1.5 mm thickness. In this case, the width of the internal space of the cassette does not vary by more than about 0.075 mm, by more than about 0.03 mm, or by more than about 0.015 mm across the top of the cassette (or the region of the cassette corresponding to where a comb is inserted).

In certain embodiments, the gel cassette has an internal gap between the front and back plates in which the internal distance between the front and back plates does not substantially vary along the upper edge of the cassette.

A gel cassette can have front and back plates constructed of any suitable material, where suitable materials include plastics, polymers, glass, ceramics, or any material that is not permeable to fluids and is non-conducting under standard electrophoresis conditions. The gel cassettes disclosed herein can be made of a polymer which is transparent to visible light, transparent to ultraviolet light, transparent to infra-red light, or transparent to both visible and ultraviolet light. Non-limiting examples of polymers used to make the gel cassettes disclosed herein are styrene acrylonitrile (SAN), polycarbonate, polystyrene, acrylic based polymers, polymethyl methacrylate (PMMA), polyethylene terephthalate (PET), glycol-modified polyethylene terephthalate (PETG), polypropylene, Acetel and copolymers thereof. The plates of the gel cassettes disclosed herein can be coated on the gel-facing side with one or more polymers such as, by way of example only, latex, thereby preventing sticking of the gel to the plates when the gel is to be removed after electrophoresis. The gel cassettes or the plates that will be attached to form a gel cassette, disclosed herein, may be fabricated using molding techniques, hot embossing methods, casting processes, thermoforming methods, stereolithography processes, machining methods and milling processes. In further or alternative embodiments, such molding techniques include injection molding and compression molding.

The front and back plates can be attached to one another (to form a gel cassette) by any feasible means including, but not limited to, being molded as a single piece along with edge pieces that connect the front and back plates at the side, being welded together (by way of example only, ultrasonic welding), being fastened together with adhesives, being thermally treated, or being held with attachment means screws, pins, snaps, or clamps. In certain embodiments of the gel cassettes disclosed herein, either or both of the front and back plates of the cassette have raised borders around the edges where the cassettes are attached, by way of example only, by welding, that provide spacers that establish the distance between the attached plates. In some embodiments, the plates so designed are welded together to specifications such that the spacer thickness establishing the distance between plates of the cassette is substantially the same from the outer edges of the cassette to at least the midpoint of the cassette along the upper edge of the cassette.

The gel cassette disclosed herein can be of any size used in any electrophoresis system. The dimensions of a gel cassette having a consistent gap width are not limiting and include, but are not limited to, gel cassette having a front plate and back plates from about 5 cm to about 30 cm in width, from about 5 cm to about 60 cm in length, and from about 1 mm to about 5 mm in plate thickness. In some embodiments, the plates of the gel cassette can be about 4 mm thick or less, about 3 mm thick or less, about 2.5 mm thick or less, about 2 mm thick or less, about 1.5 mm thick or less, or about 1 mm thick or less. In other embodiments, the back plate of a cassette is between 2.5 mm and 3 mm thick in the area containing the gel, and the front plate of a cassette is between 1.5 and 2 mm thick in the area containing the gel.

In the gel cassettes disclosed herein the front plate and back plate need not be of equal dimensions. In addition, the front plate, the back plate, or both, can be irregularly shaped along one or more sides such as, by way of example only, having at least a portion of an outer edge that is inset or curved. The gap width between plates of an assembled cassette can be from about 0.1 mm to about 10 mm, from about 0.1 mm to about 5 mm, from about 0.25 mm to about 5 mm, from about 0.25 mm to about 3 mm, from about 0.25 mm to about 2.5 mm, from about 0.25 mm to about 2 mm, from about 0.25 mm to about 1.5 mm, from about 0.25 mm to about 1 mm, from about 0.5 mm to about 5 mm, from about 0.5 mm to about 3 mm, from about 0.5 mm to about 2.5 mm, from about 0.5 mm to about 2 mm, from about 0.5 mm to about 1.5 mm, or from about 0.5 mm to about 1 mm. In illustrative embodiments, the gap width between plates of an assembled cassette is from 0.1 mm to 10 mm, from 0.1 mm to 5 mm, from 0.25 mm to 5 mm, from 0.25 mm to 3 mm, from 0.25 mm to 2.5 mm, from 0.25 mm to 2 mm, from 0.25 mm to 1.5 mm, from 0.25 mm to 1 mm, from 0.5 mm to 5 mm, from 0.5 mm to 3 mm, from 0.5 mm to 2.5 mm, from 0.5 mm to 2 mm, from 0.5 mm to 1.5 mm, or from 0.5 mm to 1 mm. The gap width can be established by spacers between the plates along the outer edges of the plates (top and bottom), or by border regions of the plates (top and bottom) that can be fastened together using welding methods (by way of example only, ultrasonic welding), thermal treatment, adhesives, gaskets, clamps, or fasteners. In certain embodiments, the cassette plates are made of one or more plastics such as, for example, and one or both of the back plate or the front plate has a raised border region that is welded or heat fused to the partner plate, and the welding process in part determines the gap width by determining the thickness of the border region that remains between the welded or heat fused plates of the cassette.

A non-limiting example of a gel cassette having a consistent internal gap between the front and back plates has front and back plates that are 10 cm×10 cm, where the front plate is about 1.75 mm thick and the back plate is about 2.55 mm thick, and the two plates are welded together such that the gap width of the cassette in the region where a comb is to be inserted to form wells is consistently about 1 mm.

Another non-limiting example of a gel cassette having a consistent internal gap between the front and back plates has front and back plates that are 10 cm×10 cm, where the front and back plates are about 1.75 mm and about 2.5 mm thick, respectively, and the plates welded together such that the gap width of the cassette is consistently about 1.5 mm.

Another non-limiting example of a gel cassette having a consistent internal gap between the front and back plates has front and back plates that are 15 cm×15 cm, where the front and back plates are about 1.75 mm and about 2.55 mm thick, respectively, and the two plates are welded together such that the gap width of the cassette in the region where a comb is to be inserted to form wells is consistently about 1 mm.

Another non-limiting example of a gel cassette having a consistent internal gap between the front and back plates has front and back plates that are 15 cm×15 cm, where the front and back plates are about 1.75 mm and about 2.55 mm thick, respectively, and the two plates are welded together such that the gap width of the cassette in the region where a comb is to be inserted to form wells is consistently about 1.5 mm.

These examples of gel cassettes having a consistent internal gap between the front and back plates are for illustrative purposes only and are not intended to be limiting in any way.

The gel cassettes disclosed herein also include gel cassettes having a consistent gap width across the upper edge of the cassette where sample loading occurs, wherein the gap width varies by less than about 5%, in some preferred embodiments by no more than about 2% or by no more than about 1%.

The gel cassettes with a consistent gap widths disclosed herein can contain a gel that comprises any suitable gel forming polymer, including, but not limited to, synthetic polymers, natural polymers and combinations thereof. Examples of such synthetic polymers include, but are not limited to, linear polyacrylamide, crosslinked polyacrylamide, or combinations thereof. Examples of such natural polymers include, but are not limited to, polysaccharides such as agarose. In certain embodiments such gels can comprise agarose, polyacrylamide, or combinations of agarose and polyacrylamide.

The gel cassettes with a consistent gap widths disclosed herein can contain any stacking gel and/or separating gel disclosed herein. In certain embodiments, the gel cassettes contain gels that includes linear acrylamide, as described herein. When present in a gel that includes a stacker, linear acrylamide can be present in the stacker and not in the separating gel. In alternate embodiments, linear acrylamide can be present in the stacker and in the separating gel. The gel can be of any polymer concentration as disclosed herein including, by way of example only, from about 0.3% to about 3% in the case of agarose, or from about 1% to about 30% acrylamide. When present, the linear acrylamide can be present at any (w/v) concentration disclosed herein including, but not limited to, from about 0.005% to about 1% and from about 0.01% to about 0.5%. The separating gel in gel cassettes with a consistent gap widths disclosed herein can be a gradient gel as disclosed herein. The separating gel in gel cassettes with a consistent gap widths disclosed herein can optionally include a stacking gel as disclosed herein, where the stacking gel has a lower concentration of gel polymer than that in the separating gel. Where combination gels are used, optimal concentrations of each component can be determined empirically or as guided by published protocols.

A gel contained in a gel cassette as described herein can also include at least one of the following: one or more buffers, salts, reducing agents, oxidizing agents, alkylating agents, denaturants, chelators, polymers, or detergents. In some embodiments, a gel contained in such cassettes is a gel to be used for separation of nucleic acids. In some embodiments, a gel contained in such cassettes is a gel to be used for polypeptide electrophoresis. In some embodiments, a gel contained in such cassettes is used for native electrophoresis of proteins, in which proteins and protein complexes are not denatured prior to or during electrophoresis. In other embodiments, a gel contained in such cassette is a gel to be used for polypeptide electrophoresis. In some embodiments, a gel contained in such cassettes is used for native electrophoresis of proteins, in which proteins and protein complexes are not denatured prior to or during electrophoresis and the gel and the running buffer(s) do not include denaturants, such as but not limited to denaturing detergents, urea, formamide, chaotropes, and the like. In a non-limiting example, Blue Native gels are used in cassettes described herein having a consistent internal gap width. In certain embodiments, the Blue Native gels have stacking gels. In other embodiments, the Blue Native gels have stacking gels that include linear acrylamide.

The buffer or buffers included in gels that are contained in gel cassettes as described herein can be any electrophoresis buffer, including but not limited zwitterionic buffers. In certain embodiments the gel buffer has a pH between 5 and 9 at ambient temperature. In certain embodiments the gel buffer has a pH between 6 and 8.5 at ambient temperature. In certain embodiments the gel buffer has a pH between 6 and 8 at ambient temperature. In certain embodiments the gel buffer has a pH between 6 and 7 at ambient temperature. In certain embodiments the gel buffer has a pH between 7 and 8 at ambient temperature. In certain embodiments the gel buffer has a pH between 5 and 9 at 25° C. In certain embodiments the gel buffer has a pH between 6 and 8.5 at 25° C. In certain embodiments the gel buffer has a pH between 6 and 8 at 25° C. In certain embodiments the gel buffer has a pH between 7 and 8 at 25° C. In certain embodiments the gel buffer has a pH between 6 and 7 at 25° C.

In certain embodiments the buffer or buffers included in gels that are contained in gel cassettes as described herein comprises a buffer having a pKa between about 5 and about 8.5 at ambient temperature. In certain embodiments the gel buffer comprises a buffer having a pKa between about 6 and about 8.5 at ambient temperature. In certain embodiments the gel buffer comprises a buffer having a pKa between about 6 and about 8 at ambient temperature. In certain embodiments the gel buffer comprises a buffer having a pKa between about 6 and about 7 at ambient temperature. In certain embodiments the gel buffer comprises a buffer having a pKa between about 7 and about 8 at ambient temperature. In certain embodiments the gel buffer comprises a buffer having a pKa between about 5 and about 8.5 at 25° C. In certain embodiments the gel buffer comprises a buffer having a pKa between about 6 and about 8.5 at 25° C. In certain embodiments the gel buffer comprises a buffer having a pKa between about 6 and about 8 at 25° C. In certain embodiments the gel buffer comprises a buffer having a pKa between about 6 and about 7 at 25° C. In certain embodiments the gel buffer comprises a buffer having a pKa between about 7 and about 8 at 25° C.

The buffer or buffers included in gels that are contained in gel cassettes as described herein include, but are not limited to, succinate, citrate, borate, maleate, cacodylate, N-(2-Acetamido)iminodiacetic acid (ADA), 2-(N-morpholino)-ethanesulfonic acid (MES), N-(2-acetamido)-2-aminoethanesulfonic acid (ACES), piperazine-N,N'-2-ethanesulfonic acid (PIPES), 2-(N-morpholino)-2-hydroxypropanesulfonic acid (MOPSO), N,N-bis-(hydroxyethyl)-2-aminoethanesulfonic acid (BES), 3-(N-morpholino)-propanesulfonic acid (MOPS), N-tris-(hydroxymethyl)-2-ethanesulfonic acid (TES), N-2-hydroxyethyl-piperazine-N-2-ethanesulfonic acid (HEPES), 3-(N-tris-(hydroxymethyl) methylamino)-2-hydroxypropanesulfonic acid (TAPSO), 3-(N,N-Bis[2-hydroxyethyl]amino)-2-hydroxypropanesulfonic acid (DIPSO), N-(2-Hydroxyethyl)piperazine-N'-(2-hydroxypropanesulfonic acid) (HEPPSO), 4-(2-Hydroxyethyl)-1-piperazinepropanesulfonic acid (EPPS), N-[Tris(hydroxymethyl)methyl]glycine (Tricine), N,N-Bis(2-hydroxyethyl)glycine (Bicine), (2-Hydroxy-1,1-bis(hydroxymethyl)ethyl)amino]-1-propanesulfonic acid (TAPS), N-(1,1-Dimethyl-2-hydroxyethyl)-3-amino-2-hydroxypropanesulfonic acid (AMPSO), tris(hydroxy methyl)amino-methane (Tris), TRIS-Acetate-EDTA (TAE), glycine, bis[2-hydroxyethyl]iminotris[hydroxymethyl]methane (BisTris), or combinations thereof. In addition, such gel buffers can include ethylene diamine tetraacetic acid (EDTA).

The concentration of the buffer or buffers included in gels that are contained in gel cassettes as described herein can be from about 10 mM to about 1.5 M. In certain embodiments the concentration can be between about 10 mM and about 1 M. In certain embodiments the concentration can be between about 20 mM and about 500 mM, and in other embodiments the concentration is between about 50 mM and about 300 mM. In certain embodiments the concentration can be between about 10 mM and about 200 mM, and in other embodiments the concentration is between about 10 mM and about 500 mM. In certain embodiments the concentration can be between about 50 mM and about 200 mM, and in other embodiments the concentration is between about 50 mM and about 500 mM. In certain embodiments the concentration can be between about 5 mM and about 200 mM, and in other embodiments the concentration is between about 5 mM and about 500 mM. In certain embodiments the concentration can be between about 5 mM and about 1 M. In certain embodiments, the concentration of the buffer or buffers included in gels that are contained in gel cassettes as described herein can be from 10 mM to 1.5 M. In certain embodiments the concentration can be between 10 mM and 1 M. In certain embodiments the concentration can be between 20 mM and 500 mM, and in other embodiments the concentration is between 50 mM and 300 mM. In certain embodiments the concentration can be between 10 mM and 200 mM, and in other embodiments the concentration is between 10 mM and 500 mM. In certain embodiments the concentration can be between 50 mM and 200 mM, and in other embodiments the concentration is between 50 mM and 500 mM. In certain embodiments the concentration can be between 5 mM and 200 mM, and in other embodiments the concentration is between 5 mM and 500 mM. In certain embodiments the concentration can be between 5 mM and 1M.

Various gel cassettes have been described in U.S. Pat. No. 7,122,104, U.S. Pat. No. 6,562,213, U.S. Pat. No. 5,582,702, U.S. Pat. No. 5,865,974, U.S. Pat. No. 6,379,516, U.S. patent application Ser. No. 11/470,308 and patent application Ser. No. 10/056,050, each of which is herein incorporated by reference in their entirety. Such cassettes including, but are not limited to, multiwell cassettes, can contain the electrophoresis gels disclosed herein and be used in the compositions and methods described herein.

The electrophoresis gels described herein can be used to separate components of a sample including, but not limited to, separating biomolecules. The methods of separating samples components on such electrophoresis gels includes, but are not limited to, applying one or more samples to an electrophoresis gel and electrophoretically separating the sample components on the electrophoresis gel. In certain embodiments, such methods include, but are not limited to, applying one or more samples comprising one or more biomolecules to an electrophoresis gel that comprises a separating gel, and electrophoretically separating one or more biomolecules or biomolecular complexes on the separating gel. In certain embodiments, such methods include, but are not limited to, applying one or more samples comprising one or more biomolecules to an electrophoresis gel that comprises a separating gel comprising linear polyacrylamide, and electrophoretically separating one or more biomolecules or biomolecular complexes on the separating gel. In certain embodiments, such methods include, but are not limited to, applying one or more samples comprising one or more biomolecules to an electrophoresis gel that comprises a stacking gel portion and a separating gel portion, and electrophoretically separating one or more biomolecules or biomolecular complexes on the separating gel. In other embodiments, such methods include, but are not limited to, applying one or more samples comprising one or more biomolecules to an electrophoresis gel that comprises a stacking gel portion that comprises linear polyacrylamide and a separating gel portion, and electrophoretically separating one or more biomolecules or biomolecular complexes on the separating gel. In certain other embodiments, such methods include, but are not limited to, applying one or more samples comprising one or more biomolecules to an electrophoresis gel that comprises a stacking gel portion and a separating gel portion, wherein both the stacking gel and the separating gel comprise linear polyacrylamide; and electrophoretically separating one or more biomolecules or biomolecular complexes on the separating gel.

In practicing the methods of the invention, wherein the stacking gel comprises linear polyacrylamide, the presence of skirting bands on the separating gel is reduced. In practicing the methods of the invention, wherein the separating gel comprises linear polyacrylamide, the presence of skirting bands on the separating gel is reduced. In practicing the methods of the invention, wherein the stacking gel and the separating gel comprise linear polyacrylamide, the presence of skirting bands on the separating gel is reduced. By "reduced" is meant the appearance, intensity, or width of skirting bands is less on electrophoresis gels having linear polyacrylamide than in electrophoresis gels without linear polyacrylamide run under the same conditions and having the same composition (except having linear polyacrylamide).

The gels used in such methods can be any electrophoresis gel described herein. In certain embodiments the gels are polyacrylamide gels. In other embodiments the gels are agarose gels, while in other embodiments the gels comprise both acrylamide and agarose. The gels used in such methods can be denaturing gels as disclosed herein, including, but not limited to, SDS polyacrylamide gels. The gels used in such methods can be non-denaturing gels as disclosed herein, including, but not limited to, blue native (BN) gels. The separating gel used in such methods can have any suitable composition. In some embodiments, the separating gel used in such methods includes linear polyacrylamide. In other embodiments, the separating gel used in such methods does not include linear polyacrylamide. In certain embodiments, the separating gel used in such methods comprises polyacrylamide, while in other embodiments the separating gel used in such methods comprises both polyacrylamide and linear polyacrylamide. In some embodiments, the separating gel used in such methods is a gradient gel. In certain embodiments, the electrophoresis gels used in such methods are multiwell gels, in which two or more samples, one or more samples, or multiple loadings of the same sample are electrophoresed simultaneously. In certain embodiments, the electrophoresis gels used in such methods are multiwell gels, in which one or more molecular weight standards along with two or more samples, one or more samples, or multiple loadings of the same sample are electrophoresed simultaneously.

Native or non-denaturing gels used in the methods disclosed herein are run without denaturing agents such as, for example, protein-denaturing detergents or chaotropes in the gel or in the running buffer(s). The native gels used in the methods disclosed herein include, but are not limited to, blue native (BN) gels. The use of blue native gels, in which the cathode buffer, the protein sample buffer, or both, contain Coomassie G-250 has been described in Schagger H and von Jagow G (1991) "Blue native electrophoresis for isolation of membrane protein complexes in enzymatically active form" *Anal. Biochem.* 199: 223-231; Schagger H, Cramer W A, and von Jagow G (1994) "Analysis of molecular masses and oligomeric states of protein complexes by blue native electrophoresis and isolation of membrane protein complexes by two-dimensional native electrophoresis" *Anal. Biochem.* 217: 220-230; and Schagger H (2001) "Blue-native gels to isolate protein complexes from mitochondria" *Methods Cell Biol.* 65: 231-244. The Coomassie G-250 binds proteins in their native state, thereby conferring a negative charge to the proteins. The negatively charged Coomassie stained proteins then migrate to the anode at a velocity that is proportional to their charge and molecular weight.

The biomolecules separated on an electrophoresis gel described herein and using the methods described herein can be any biomolecule, including, but not limited to, proteins, nucleic acids, polysaccharides, lipids, and other macromolecules. In certain embodiments the biomolecules separated on an electrophoresis gel described herein and using the methods described herein are proteins, nucleic acids, or biomolecular complexes that include proteins or nucleic acids. By way of example only, such biomolecular complexes can be any combination of associated proteins, peptides, nucleic acids, and polysaccharides. In exemplary embodiments, the biomolecules or complexes separated on an electrophoresis gel that comprises linear polyacrylamide in the stacking portion of the gel are proteins or molecular complexes that include proteins. In certain embodiments the electrophoresis gel has two or more wells for electrophoresis of at least two standards or at least one sample and at least one molecular weight standard. In exemplary embodiments, the biomolecules or complexes separated on an electrophoresis gel, that is contained in a gel cassette having a consistent internal gap as disclosed herein, are proteins or molecular complexes that include proteins.

The one or more samples, or two or more replicates of the same sample, applied to the electrophoresis gel can be any samples that include biomolecules, and can be environmental samples, tissue samples, cell extracts or fractions, etc. The samples can be crude samples such as lysates, fractionated samples, or partially or substantially processed or purified samples. Prior to loading on an electrophoresis gel, a sample can be treated with solubilizers, reducing agents, denaturing agents or treatments, detergents, chaotropic agent, or other sample preparation agents. In the case of Blue Native gel electrophoresis, proteins and protein complexes are not denatured prior to electrophoresis, but may be exposed to solubilizers such as, for example, non-denaturing detergents.

The methods, gels and gel cassettes described herein can be used to electrophoretically separate biomolecules and/or biomolecular complexes. However, general electrophoresis methods and parameters, such as sample loading and electrophoresis run time are known in the art and are well within the capabilities of a killed artisan. In addition, apparatuses designed to hold gel assemblies, gel cassettes and running buffers, during electrophoresis are well known in the art and widely available commercially, including but not limited to, the SureLock™ mini-cell electrophoresis apparatus (Invitrogen Corp, Carlsbad, Calif.). Such apparatuses can be used with the methods, gels and gel cassettes described herein.

Although electrophoresis conditions can be determined by a practitioner guided by protocols known in the art. The electrophoretic separations disclosed herein can be achieved using constant voltage, pulsed voltage, step-gradient voltage, constant current, pulsed current, step-gradient current, constant power, step-gradient power or pulsed power. Subsequently, the applied electric field (V/cm) in the methods disclosed herein can be constant or pulsed. It is understood that the magnitude of the applied voltage, applied current or applied power to achieve the electric fields ranges provided below will vary depending on the dimensions of the electrophoresis cassette and buffer conductivity. By way of example only, the applied voltage can range from 5V to 2000V, and in certain embodiments the applied voltage can range from 5V to 1000V, 5V to 500V, 5V to 250V, or 5V to 100V. In other embodiments, the applied voltage can range from about 10 to about 1,000 V, from about 25 to about 750 V, or from about 40 to about 300 V. By way of example only, the applied current can range from 5 mA to 400 mA, and in certain embodiments the applied current can range from 5 mA to 200 mA, 5 mA to 100 mA, 5 mA to 50 mA, or 5 mA to 25 mA. In one embodiment the applied current can be 15 mA. By way of example only, the applied current can range from 5 mA to 400 mA, and in certain embodiments the applied power can range from 25 mW to 400 W, 25 mW to 100 W, 25 mW to 50 W, or 25 mW to 25 W. In one embodiment the applied power can be 4.5 W. In addition the polarity of the applied voltage (constant or pulsed) can be positive or negative, and the polarity of the applied current (constant or pulsed) can be positive or negative.

In certain embodiments the magnitude of the constant electric field applied is between 1 V/cm and 100 V/cm. In certain embodiments the magnitude of the constant electric field applied is between 1 V/cm and 50 V/cm. In certain embodiments the magnitude of the constant electric field applied is between 1 V/cm and 25 V/cm. In certain embodiments the magnitude of the constant electric field applied is between 1 V/cm and 15 V/cm. In certain embodiments the magnitude of the constant electric field applied is between 1 V/cm and 10 V/cm.

For the application of a step-gradient voltage, the step profile can be a single step, two steps, or greater than two steps. The step voltage is applied to a constant baseline electric field, established by applying a baseline voltage, and the magnitude of this baseline electric field is from 0 V/cm to 100 V/cm. In certain embodiments the magnitude of this baseline electric field is from 0 V/cm to 50 V/cm. In certain embodiments the magnitude of this baseline electric field is from 0 V/cm to 25 V/cm. In certain embodiments the magnitude of this baseline electric field is from 0 V/cm to 10 V/cm. In certain embodiments the magnitude of the baseline voltage is from 0V to 1000V, while in other embodiments the magnitude of the baseline voltage is from 0V to 500V. In certain embodiments the magnitude of the baseline voltage is from 0V to 200V, while in other embodiments the magnitude of the baseline voltage is from 0V to 100V. In certain embodiments the magnitude of the baseline voltage is from 0V to 50V, while in other embodiments the magnitude of the baseline voltage is from 0V to 10V. The magnitude of the voltage step applied to the baseline voltage can be from 10V to 2000V, while in other embodiments the voltage step is from 10V to 1000V. In certain embodiments the magnitude of the voltage step applied to the baseline voltage is from 10V to 500V, while in other embodiments the magnitude of the voltage step is from 10V to 200V. In certain embodiments the magnitude of the voltage step applied to the baseline voltage is from 10V to 100V, while in other embodiments the magnitude of the voltage step is from 10V to 50V. For multiple steps, such as two or more steps, the magnitude of each step can be symmetric (i.e. the same), or the magnitude of each step can be asymmetric (i.e. different). In certain embodiments a two step symmetric step-gradient voltage profile is a first 50V step applied to a 0V baseline, followed by another 50V step. In certain embodiments a two step asymmetric step-gradient voltage profile is a first 50V step applied to a 0V baseline, followed by a 450V step. In certain embodiments a two step asymmetric step-gradient voltage profile is a first 50V step applied to a 0V baseline, followed by a 500V step. In other embodiments a two step asymmetric step-gradient voltage profile is a first 75V step applied to a 0V baseline, followed by a 175V step. In other embodiments a two step asymmetric step-gradient voltage profile is a first 75V step applied to a 0V baseline, followed by a 250V step. A single step, or independently each step of a multiple step-gradient, can be run for from about 5 minutes to about 500 minutes, depending on the magnitude of the applied voltages. In certain embodiments the step run times can be from about 5 minutes to about 150 minutes. In certain embodiments the step run times can be from about 5 minutes to about 100 minutes. In certain embodiments the step run times can be from about 5 minutes to about 60 minutes. In certain embodiments the step run times can be from about 5 minutes to about 30 minutes. In certain embodiments for a two step asymmetric step-gradient voltage profile the first step is applied for 15 minutes and the second step is applied for 45 minutes. In certain embodiments for a two step asymmetric step-gradient voltage profile the first step is applied for 15 minutes and the second step is applied for 50 minutes. In certain embodiments for a two step asymmetric step-gradient voltage profile the first step is applied for 15 minutes and the second step is applied for 55 minutes. In certain embodiments for a two step asymmetric step-gradient voltage profile the first step is applied for 15 minutes and the second step is applied for 60 minutes. In certain embodiments for a two step asymmetric step-gradient voltage profile the first step is applied for 15 minutes and the second step is applied for 65 minutes.

For the application of a step-gradient current profile, the step profile can be a single step, two steps, or greater than two steps. The step current is applied to a constant baseline electric field, established by applying a baseline current, and the magnitude of this baseline electric field is from 0 V/cm to 100 V/cm. In certain embodiments the magnitude of this baseline electric field is from 0 V/cm to 50 V/cm. In certain embodiments the magnitude of this baseline electric field is from 0 V/cm to 25 V/cm. In certain embodiments the magnitude of this baseline electric field is from 0 V/cm to 10 V/cm. In certain embodiments the magnitude of the baseline current is from 0 mA to 10 mA, while in other embodiments the magnitude of the baseline current is from 0 mA to 5 mA. In certain embodiments the magnitude of the baseline current is from 0 mA to 2 mA, while in other embodiments the magnitude of the baseline current is from 0 mA to 1 mA. In certain embodiments the magnitude of the baseline current is from 0 mA to 0.5 mA. The magnitude of the current step applied to a baseline current can be from 0.5 mA to 100 mA, while in other embodiments the current step is from 0.5 mA to 50 mA. In certain embodiments the magnitude of the current step applied to a baseline current is from 0.5 mA to 25 mA, while in other embodiments the magnitude of the current step is from 0.5 mA to 10 mA. In certain embodiments the magnitude of the current step applied to the baseline current is from 0.5 mA to 5 mA, while in other embodiments the magnitude of the current step is from 0.5 mA to 2 mA. For multiple steps, such as two or more steps, the magnitude of each step can be symmetric (i.e. the same), or the magnitude of each step can be asymmetric (i.e. different). In certain embodiments a two step symmetric step-current current profile is a first 7 mA step applied to a 0 mA baseline, followed by another 7 mA step. In certain embodiments a two step asymmetric step-gradient current profile is a first 1 mA step applied to a 0 mA baseline, followed by a 14 mA step. A single step, or independently each step of a multiple step-gradient, can be run for from about 5 minutes to about 500 minutes, depending on the magnitude of the applied current. In certain embodiments the step run times can be from about 5 minutes to about 150 minutes. In certain embodiments the step run times can be from about 5 minutes to about 100 minutes. In certain embodiments the step run times can be from about 5 minutes to about 60 minutes. In certain embodiments the step run times can be from about 5 minutes to about 30 minutes. In certain embodiments for a two step asymmetric step-gradient current profile the first step is applied for 15 minutes and the second step is applied for 45 minutes. In certain embodiments for a two step asymmetric step-gradient current profile the first step is applied for 15 minutes and the second step is applied for 50 minutes. In certain embodiments for a two step asymmetric step-gradient current profile the first step is applied for 15 minutes and the second step is applied for 55 minutes. In certain embodiments for a two step asymmetric step-gradient current profile the first step is applied for 15 minutes and the second step is applied for 60 minutes. In certain embodiments for a two step asymmetric step-gradient current profile the first step is applied for 15 minutes and the second step is applied for 65 minutes.

For the application of a step-gradient power profile, the step profile can be a single step, two steps, or greater than two steps. The step current is applied to a constant baseline electric field, established by applying a baseline power level, and the magnitude of this baseline electric field is from 0 V/cm to 100 V/cm. In certain embodiments the magnitude of this baseline electric field is from 0 V/cm to 50 V/cm. In certain embodiments the magnitude of this baseline electric field is from 0 V/cm to 25 V/cm. In certain embodiments the magnitude of this baseline electric field is from 0 V/cm to 10 V/cm. In certain embodiments the magnitude of the baseline power is from 0 W to 10 W, while in other embodiments the magnitude of the baseline power is from 0 W to 5 W. In certain embodiments the magnitude of the baseline power is from 0 W to 2 W, while in other embodiments the magnitude of the baseline current is from 0 W to 1 W. In certain embodiments the magnitude of the baseline power is from 0 W to 0.5 W. The magnitude of the power step applied to a baseline can be from 0.5 W to 10 W, while in other embodiments the power step is from 0.5 W to 5 W. In certain embodiments the magnitude of the power step applied to a baseline is from 0.5 W to 2 W, while in other embodiments the magnitude of the power step is from 0.5 mA to 1 W. For multiple steps, such as two or more steps, the magnitude of each step can be symmetric (i.e. the same), or the magnitude of each step can be asymmetric (i.e. different). In certain embodiments a two step symmetric step-power profile is a first 1.5 W step applied to a 0 W baseline, followed by another 1.5 W step. In certain embodiments a two step asymmetric step-gradient power profile is a first 0.5 W step applied to a 0 mA baseline t, followed by a 3 W step. A single step, or independently each step of a multiple step-gradient, can be run for from about 5 minutes to about 500 minutes, depending on the magnitude of the applied current. In certain embodiments the step run times can be from about 5 minutes to about 150 minutes. In certain embodiments the step run times can be from about 5 minutes to about 100 minutes. In certain embodiments the step run times can be from about 5 minutes to about 60 minutes. In certain embodiments the step run times can be from about 5 minutes to about 30 minutes. In certain embodiments for a two step asymmetric step-gradient power profile the first step is applied for 15 minutes and the second step is applied for 45 minutes. In certain embodiments for a two step asymmetric step-gradient power profile the first step is applied for 15 minutes and the second step is applied for 50 minutes. In certain embodiments for a two step asymmetric step-gradient power profile the first step is applied for 15 minutes and the second step is applied for 55 minutes. In certain embodiments for a two step asymmetric step-gradient power profile the first step is applied for 15 minutes and the second step is applied for 60 minutes. In certain embodiments for a two step asymmetric step-gradient power profile the first step is applied for 15 minutes and the second step is applied for 65 minutes.

The profile of the pulsed electric field (applied voltage, current or power) can be a square wave, triangular wave or sine wave, and such profiles can be symmetric or asymmetric. The pulsed electric field is applied to a constant baseline electric field and the magnitude of this baseline electric field is from 0 V/cm to 100 V/cm. In certain embodiments the magnitude of this baseline electric field is from 0 V/cm to 50 V/cm. the magnitude of this baseline electric field is from 0 V/cm to 25 V/cm. the magnitude of this baseline electric field is from 0 V/cm to 10 V/cm. In certain embodiments the magnitude of the pulsed electric field applied in addition to the baseline electric field is between 1 V/cm and 100 V/cm. In certain embodiments the magnitude of the pulsed electric field applied in addition to the baseline electric field is between 1 V/cm and 50 V/cm. In certain embodiments the magnitude of the pulsed electric field applied in addition to the baseline electric field is between 1 V/cm and 25 V/cm. In certain embodiments the magnitude of the pulsed electric field applied in addition to the baseline electric field is between 1 V/cm and 10 V/cm.

For pulsed electric fields which are symmetric square waves the time the pulsed electric field is applied in addition to the baseline electric field (ON) is the same as the time that the pulsed electric field is not applied (OFF). In certain embodiments the ON and OFF times are between 1 ms and 60 seconds. For pulsed electric fields which are asymmetric square wave pulsed electric fields have the time the pulsed electric field is applied in addition to the baseline electric field (ON) is not the same as the time that the pulsed electric field is not applied (OFF). In certain embodiments the ON time is independently between 1 ms and 60 seconds, and the OFF time is independently between 1 ms and 60 seconds.

For pulsed electric fields which are symmetric triangular waves the voltage ramp rate (V/s) up to the maximum electric field applied is the same as the time that the voltage ramp rate (V/s) down to the baseline electric field applied. In certain embodiments the voltage ramp up and the voltage ramp down are between 10 mV/s and 100 V/s. For pulsed electric fields which are asymmetric triangular waves the voltage ramp rate (V/s) up to the maximum electric field applied is not the same as the time that the voltage ramp rate (V/s) down to the baseline electric field applied. In certain embodiments the voltage ramp up is independently between 10 mV/s and 100 V/s and the voltage ramp down is independently between 10 mV/s and 100 V/s.

For pulsed electric fields which are symmetric sine waves the period and frequency are constant, and the minimum electric field of the sine wave is the same as the baseline electric field applied. For pulsed electric fields which are asymmetric sine waves the period and frequency are modulated, and the minimum electric field of the sine wave is the same as the baseline electric field applied.

The electrophoresis runs of the methods disclosed herein can be performed at room temperature, ambient temperature, or at a higher or lower temperature. By way of example only it may be desirable for users to run their gels in a cold room with pre-chilled buffers or at room temperature with pre-chilled buffers. In certain embodiments the electrophoretic runs are performed at lower temperatures include, but are not limited to, temperatures from about 1° C. to about 10° C. For low temperature runs, it can in some cases be preferable to run the gel at a higher voltage at the end of the run.

The methods disclosed herein also include detecting one or more bands on the electrophoresed gel that comprises a biomolecule. One or more biomolecules or biomolecular complexes can be stained or labeled before, during, or after electrophoresis using techniques that are well known in the art. The bands can be observed using light boxes, scanners, or by the naked eye without special equipment. Optionally, the migration distance of one or more bands of a sample can be determined. Optionally, molecular weight markers can be electrophoresed on the same gel that the sample is electrophoresed on, by applying a set of one or more molecular weight markers on the gel to electrophoresis alongside the one or more samples. The molecular weight of one or more bands from the sample can be estimated or calculated by comparing the migration of the band with that of one or more bands of the molecular weight markers. The one or more bands can represent, for example, proteins, protein complexes, nucleic acids, or nucleic acid-protein complexes.

Visualization of the sample bands in the electrophoresis gel can be achieved by illuminating the electrophoresis gel with light of appropriate wavelength(s) to allow observation of dyes, stains or other indicators associated with the sample bands. In certain embodiments of the visualization methods, used in the methods disclosed herein, the dyes, stains or other indicators are added to the sample prior to loading in the electrophoresis gel. In other embodiments, the dyes, stains or other indicators are added to the loading well or loading wells prior to addition of the sample to loading wells of the electrophoresis gel, while in other embodiments the dyes, stains or other indicators are added to the loading well or loading wells after to addition of the sample loading wells of the electrophoresis gel. Alternatively, in certain embodiments of the visualization methods, used in the methods disclosed herein, the dyes, stains or other indicators are added to the electrophoresis gel whereby they become associated with the sample components during electrophoretic migration. In still other embodiments of the visualization methods, used in the methods disclosed herein, the dyes, stains or other indicators are covalently attached to the sample components.

The systems, dyes and stains used for visualization can be fluorescent or non-fluorescent. Non-limiting examples of the systems, dyes and stains used in the methods disclosed herein are silver staining or Coumassie Blue stain.

The light used for visualization can be monochromatic or polychromatic. By way of example only, polychromatic light can be white light, UV light or infra-red light, while monochromatic light can be achieved using lasers or Light Emitting Diodes (LED's), or by specific spectral filtering of sources such as white light, UV light or infra-red light. It would be understood that the desired wavelength of such monochromatic light depends on the specific spectral characteristics of the dye or stain used, and the skilled artisan will know the methods to obtain such monochromatic light.

In certain embodiment visualization is performed in a stand alone "light box" in which the electrophoresis cassette is placed during or after electrophoretic separation of the sample. In such light boxes the electrophoresis cassette can be illuminated from above or below. Monitoring can be achieved using a CCD camera or a video camera, or by direct observation of the user. In other embodiments of such visualization methods an electrophoresis/monitoring apparatus is used in which the monitoring means (CCD camera or a video camera, or by direct observation) and the means for application of the electric field or fields are combined into one apparatus.

Figure 1:
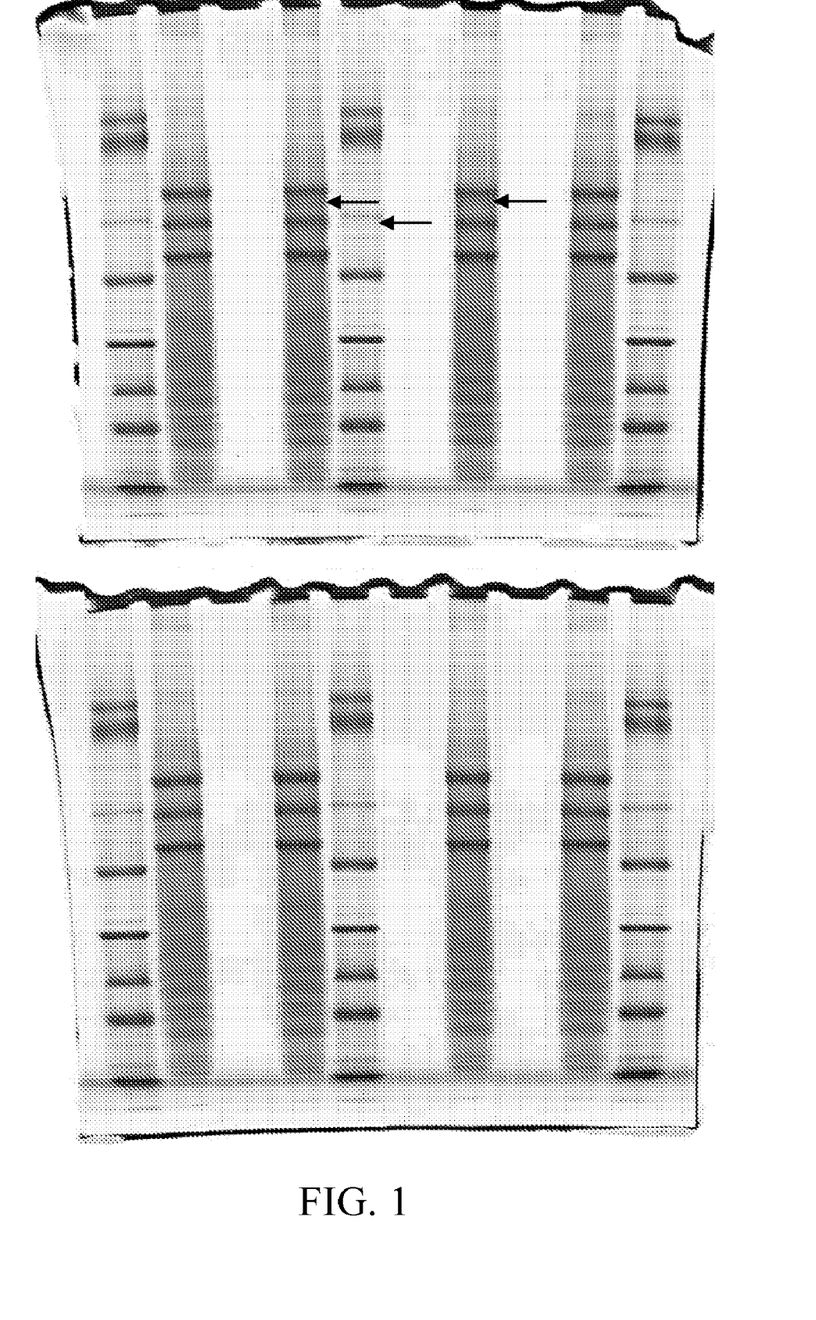
FIG. 1 shows 3-12% Blue Native gradient gels made without (top gel) or with (bottom gel) 0.05% linear acrylamide in the stacking gel.

FIG. 1 compares electrophoretic separation of proteins and protein complexes on a gel that includes linear acrylamide in the stacker and a gel that does not include linear acrylamide in the stacker. The electrophoresis gels used were 3-12% Blue Native gradient gels without linear acrylamide in the stacking gel (top gel) or with 0.05% linear acrylamide in the stacking gel (bottom gel). Gels were run for 90 minutes at 150V using 50 mM BisTris, 50 mM Tricine running buffer (0.02% Coomassie G-250 in cathode buffer only) and stained with colloidal Coomassie. Lanes 1, 5, and 10 were loaded with 5 uL of unstained native standards (Invitrogen, Carlsbad, Calif.); Lanes 2, 4, 7, and 9 were loaded with 4 uL of bovine mitochondrial extract solubilized in 1% dodecylmaltoside. Arrows indicate skirting artifacts (present in the top gel only). The presence of linear acrylamide in the stacking gel reduced the skirting effects as observed in the electrophoresis gel without the linear acrylamide in the stacking gel.

EXAMPLES

Example 1

Native Protein/Protein Complex Gel Electrophoresis

Gel and Cassettes:

3-12% polyacrylamide gradient gels were poured comprising acrylamide/bisacrylamide in a ratio of 25.5:1 in BisTris-Cl, pH 7.0 and 0.3 mM CHAPS detergent. The stacker was 3% acrylamide/bisacrylamide in a ratio of 25.5:1 and 0.05% w/v linear acrylamide (600,000 to 1,000,000 Daltons). A first gel was poured in a cassette in which the measurement of the gap in the middle of the cassette along the upper edge was 0.923 mm, and a second gel was poured in a cassette having a gap of 0.991 mm in the middle of the cassette along the upper edge. The interplate gaps at the left and right edges of these cassettes were between 1.01 mm and 1.02 mm, therefore the first gel cassette has a narrower middle region compared with the second gel cassette.

Sample Preparation:

Bovine mitochondria were isolated as described previously (Rice, J. E. & Lindsay, J. G. (2002) "Subcellular fractionation of mitochondria" in *Subcellular Fractionation: A Practical Approach*, Edited by Graham, J. M. & Rickwood D., Oxford University Press, New York, pp. 107-115). Isolated mitochondria in TESS buffer (250 mM sucrose, 1 mM succinate, 0.2 mM EDTA, 10 mM Tris pH 7.8 at 4° C.) were stored at −80° C. in 250 uL aliquots. Aliquots were thawed on ice before extracting mitochondrial proteins in cold 1× Sample Buffer containing 1% dodecylmaltoside or 2% digitonin, 50 mM BisTris-CL, pH, 7.0, 50 mM NaCl, 10% w/v glycerol and 0.001% Ponceau S. Mitochondria were dissolved in buffer by pipetting up and down through a yellow pipette tip and by inversion. Mitochondrial extracts were incubated on ice for 15 minutes before centrifuging 30 minutes at 20,000×g and 4° C. Pellets were discarded and supernatants were aliqotted and stored at −80° C. until used. Before loading onto the gel, 5% G-250 sample additive that included 5% Coomassie G-250 and 20.1% NDSB201 was added to the sample so that the final concentration of the G-250 was one-fourth that of the detergent concentration in the sample. The 5% G-250 sample additive was added to the samples while they were on ice and just before loading onto the gel. For samples that did not contain detergent, no 5% G-250 sample additive was used.

Five microliters of unstained native protein standards comprising IgM, Apoferritin, B-Phycoerythrin, Lactate Dehydrogenase, Bovine Serum Albumin, and Soybean Trypsin Inhibitor used as molecular weight markers on the gels.

Loading Samples onto NativePAGE™ Gels:

Native gels were prepared for sample application by removing the comb and tape then rinsing the sample wells once with cathode buffer before again filling the sample wells with cathode buffer. Samples were loaded onto the gels either outside of the SureLock™ mini-cell electrophoresis apparatus (Invitrogen Corp, Carlsbad Calif.) or in the mini-cell before running buffer was added. Samples were loaded by underlaying the sample beneath the cathode buffer by delivering the sample to the bottom of the well in as thin a layer as possible. An effort was also made to minimize the amount of time between loading sample onto the gels and beginning electrophoresis.

Running NativePAGE™ Gels:

Running buffers were prepared as shown in the following table.

TABLE 1

Running Buffers for Native Gel Electrophoresis

| Component | Anode Buffer | Dark Blue Cathode Buffer | Light Blue Cathode Buffer |
|---|---|---|---|
| Running Buffer (20X) | 30 mL | 10 mL | 10 mL |
| Cathode Additive (20X) | 0 mL | 10 mL | 1 mL |
| Ultrapure water | 570 mL | 180 mL | 189 mL |

20× Running Buffer was 1 M BisTris, 1 M Tricine, pH 7.5-7.65. Cathode additive was 0.4% Coomassie G-250 in water.

Figure 3:
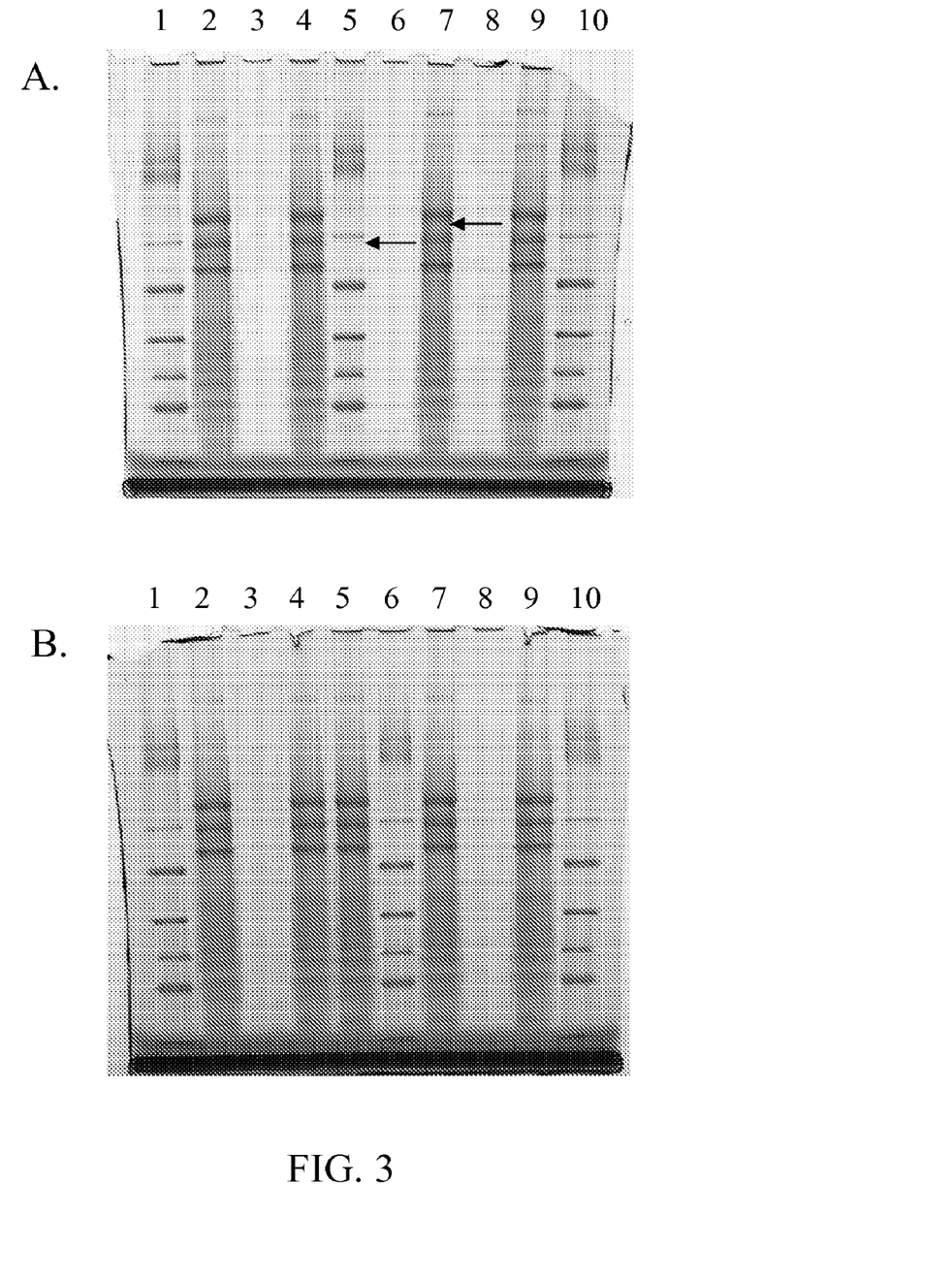
FIG. 3 depicts sample proteins/protein complexes and marker proteins separated on a gel run in a cassette that did not have a consistent gap width between plates (A) and a gel run in a cassette that did have a consistent gap width between plates (B).

The type of cathode buffer used depended on the application performed. Table 2 details the various cathode buffers used. By way of example only, the dark blue cathode buffer contained 0.02% G-250 and was used in native electrophoresis runs where samples that contain detergent were used, as shown in FIG. 3. A light blue cathode buffer containing 0.002% G-250 and was used in native electrophoresis runs where samples did not contain detergent, or where the dark blue cathode buffer would interfere with downstream applications. Downstream applications that benefit from the use of the light blue cathode buffer are western blotting, silver staining, and 2-dimensional native-SDS PAGE. For native electrophoresis runs of detergent-containing samples intended for downstream processing requiring light blue cathode buffer, the run was started with the dark blue cathode buffer and after the dye-migration front was one-third of the way down the gel the run was paused, the dark blue cathode buffer removed with a serological pipette and replaced by the light blue cathode buffer before resuming the run.

Staining NativePAGE™ Gels:

After running the native gels they were deeply blue and some highly abundant protein bands were visible; however, further staining of the gel was necessary. At the end of the run, all proteins were still in their native folded state, and in order to provide the most sensitive staining the proteins were at least partially denatured to expose more hydrophobic sites for dye-binding according to the follow method.

Coomassie G-250 Long Protocol, High Sensitivity Staining:

The gels were placed in 100 mL fix solution (40% methanol, 10% acetic acid) and microwaved 45 seconds and shake for 15-30 minutes. The fix step was repeated once for the 3-12% gels. The fix solution was decanted, and 100 mL stain solution was added from the Colloidal Blue Staining Kit (Invitrogen Corp., Carlsbad, Calif.; 55 mL water, 20 mL methanol, 20 mL stainer A, 5 mL stainer B) and the gels were incubated overnight with shaking Stain solution was decanted, and 100 mL 8% acetic acid was added. The gels were incubated with shaking for 5 minutes (this removes any G-250 precipitated on the surface of the gel or staining vessel). The acetic acid was then decanted, and 100 mL distilled water was added and the gels were shaken until desired background level was obtained.

The results, typified in FIG. 3, shows that the cassettes with middle gap measurements that were similar to their upper gap measurements produced non-skirting gels, while cassettes with middle gap measurements significantly smaller than their upper gap measurements produced skirting gels. Skirting artifacts in gel A are indicated with arrows.

While the invention has been disclosed in connection with illustrative embodiments, it is not intended to limit the scope of the invention to the particular form set forth, but on the contrary, it is intended to cover such alternatives, modifications, and equivalents as may be included within the spirit and scope of the invention as defined by the appended claims.

It should be understood that the foregoing description is only illustrative of the invention. Headings are for convenience only and are not intended to limited disclosure falling under a heading to only that heading. Various alternatives and modifications can be devised by those skilled in the art without departing from the invention. Accordingly, the present invention is intended to embrace all such alternatives, modifications and variances which fall within the scope of the appended claims.

All publications, patents and patent applications mentioned in this specification are herein incorporated by reference in their entirety to the same extent as if each individual publication, patent or patent application was specifically and individually indicated to be incorporated by reference.

TABLE 2

Cathode Buffers for Native Gel Electrophoresis

| | Application: | | | | |
|---|---|---|---|---|---|
| | Detergent sample, Coomassie stain | Non-detergent samples, Coomassie stain | Detergent samples, western blotting or 2D | Detergent samples Silvers stain | Non-detergent samples, western blotting or 2D |
| Cathode Buffer: | Dark Blue | Dark Blue or Light Blue | Dark Blue then Light Blue | Light Blue | Light Blue |

Electrophoresis was performed at 150V. The current limit was set at 15 mA per gel. The run times for 3-12% gels were typically 90-100 minutes and the run times for 4-16% gels were typically 105-120 minutes when running at room temperature with room temperature buffers.

What is claimed is:

1. A polyacrylamide gel for the separation of biomolecules, comprising a stacking gel and a separating gel, wherein the stacking gel comprises linear, non-crosslinked polyacrylamide at a concentration of from 0.005% to 1%, and wherein the separating gel does not comprise linear, non-crosslinked polyacrylamide.

2. The polyacrylamide gel of claim 1, wherein the polyacrylamide and bisacrylamide concentration of the stacking gel is between 2% and 6%, and is optionally between 2.5% and 5%.

3. The polyacrylamide gel of claim 2, wherein the concentration of the linear, non-crosslinked polyacrylamide of the stacking gel is from 0.01% to 0.5%, and optionally from 0.02% to 0.1%.

4. The polyacrylamide gel of any of claim 1, wherein the polyacrylamide gel comprises SDS (sodium dodecyl sulfate).

5. The polyacrylamide gel of any of claim 1, wherein the polyacrylamide gel is a non-denaturing gel, wherein optionally the non-denaturing gel is a gradient gel or a Blue Native Gel.

6. A cassette for performing native gel electrophoresis, wherein the cassette contains a polyacrylamide gel of according to claim 1 and has a consistent gap width across its upper edge.

7. The cassette of claim 6, wherein the cassette is plastic.

8. The cassette of claim 6, wherein the cassette is made by attaching a front plate to a back plate by one or more of the following: being moulded as a single piece along with edge pieces that connect the front and back plates at the side; being welded together; being fastened together with adhesives; being thermally treated; or being held with attachment means screws, pins, snaps, or clamps.

9. The cassette of claim 6, wherein the cassette has a gap width across its upper edge in the range from 0.1 millimeters to 5 millimeters.

10. The cassette of claim 6, wherein the gap width varies by less than 5%, preferably by less than 2%.

11. A method of separating biomolecules on an electrophoresis gel, comprising:
applying one or more samples comprising one or more biomolecules to a polyacrylamide gel of according to claim 1; and
electrophoretically separating one or more biomolecules on the gel.

12. The method of claim 11, wherein the gel is a multiwell gel.

13. The method of claim 11, further comprising applying one or more molecular weight marker sets to the electrophoresis gel, optionally further comprising estimating or calculating the molecular weight of one or more biomolecules or biomolecular complexes on the electrophoresis gel.

14. The method of claim 11, further comprising staining the gel.

15. The method of claim 11, wherein the polyacrylamide gel is within a cassette that has a consistent gap width across its upper edge.

* * * * *